(12) United States Patent
Johansson et al.

(10) Patent No.: US 6,313,132 B1
(45) Date of Patent: Nov. 6, 2001

(54) THERAPEUTICALLY ACTIVE DIARYLPROPYLAMINES; THEIR PHARMACEUTICALLY ACCEPTABLE SALTS; A METHOD FOR THEIR PREPARATION AND METHOD FOR THEIR USE

(75) Inventors: Rolf Johansson, Huddinge; Martin Haraldsson, Taby; Erik Ringberg, Uppsala; Ian Vagberg, Sollentuna; Katarina Beierlein, Uppsala; Rikard Emond, Saltsjobaden; Birger Sjoberg, Sollentuna, all of (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/381,868

(22) PCT Filed: Mar. 26, 1998

(86) PCT No.: PCT/SE98/00556

§ 371 Date: Sep. 27, 1999

§ 102(e) Date: Sep. 27, 1999

(87) PCT Pub. No.: WO98/43942

PCT Pub. Date: Oct. 8, 1998

(51) Int. Cl.⁷ ...................... A61K 31/135; A61K 31/33; A61P 13/10; C07C 211/06; C07C 215/54

(52) U.S. Cl. .................. 514/277; 514/365; 514/372; 514/375; 514/379; 514/315; 514/396; 514/408; 514/438; 514/471; 514/603; 546/184; 546/290; 546/348; 548/202; 548/217; 548/241; 548/346.1; 548/578; 549/74; 549/491; 564/316

(58) Field of Search ............................ 564/316; 514/603

(56) References Cited

U.S. PATENT DOCUMENTS

| 3,238,242 | * | 3/1966 | Harsanyi et al. ............ 564/316 X |
| 3,274,248 | * | 9/1966 | Harsanyi et al. ............ 564/316 |
| 3,446,901 |   | 5/1969 | Jones et al. ................. 424/330 |
| 4,988,730 | * | 1/1991 | Korbonits et al. ............ 514/466 |
| 5,382,600 | * | 1/1995 | Jonsson et al. .............. 514/603 |

FOREIGN PATENT DOCUMENTS

| 1181232 | * | 11/1964 | (DE) . |
| 1216318 |   | 5/1966 | (DE) . |
| 1216318B1 |   | 5/1966 | (DE) . |
| 1169944 |   | 11/1969 | (GB) . |
| 1169944A |   | 11/1969 | (GB) . |
| 1169945 |   | 11/1969 | (GB) . |
| 1169945A |   | 11/1969 | (GB) . |
| 0215495 |   | 1/1961 | (SE) . |
| 89 06644 |   | 7/1989 | (WO) . |
| 89-000556 |   | 7/1989 | (WO) . |
| 94 11337 |   | 5/1994 | (WO) . |
| 94-011337 |   | 5/1994 | (WO) . |

\* cited by examiner

*Primary Examiner*—Jane C. Osowecki
(74) *Attorney, Agent, or Firm*—Birch, Stewart, Kolasch & Birch, LLP

(57) ABSTRACT

The invention relates to novel compounds of Formula (I) wherein $R^1$, $R^2$, $R^3$, $R^4$, $R^5$, $R^6$, $R^7$ and Ar are as defined in claim 1, their salts with physiologically acceptable acids and, when the compounds can be in the form of optical isomers, the racemic mixture and the individual enantiomers. The compounds have anticholinergic activity, and the invention also relates to the compounds of Formula (I), the use of the compounds of Formula (I) for preparing anticholinergic drugs, the use of the compounds of Formula (I) for treating urinary tract incontinence, and methods for preparing the compounds of Formula (I).

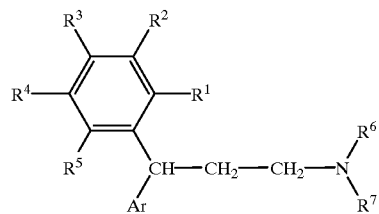

33 Claims, No Drawings

THERAPEUTICALLY ACTIVE DIARYLPROPYLAMINES; THEIR PHARMACEUTICALLY ACCEPTABLE SALTS; A METHOD FOR THEIR PREPARATION AND METHOD FOR THEIR USE

This application is the national phase under 35 U.S.C. §371 of PCT International Application Ser. No. PCT/SE98/00556 which has an International filing date of Mar. 26, 1998, which designate the United States of America.

TECHNICAL FIELD

The present invention relates to novel therapeutically active compounds, methods for their preparation, pharmaceutical compositions containing the novel compounds, and the use of the compounds for preparing drugs.

BACKGROUND OF THE INVENTION

WO 89/06644 and WO 94/11337 disclose tertiary 3,3-diphenylpropylamines having anticholinergic activity, especially for the treatment of urinary incontinence. SE-A-215499 discloses secondary 3,3-diphenylpropylamines having an advantageous effect on the heart and circulation. U.S. Pat. No. 3,446,901, GB-A-1,169,944 and GB-A-1,169,945 disclose 3,3-diphenylpropylamines having antidepressant activity. DE-B1-1216318 discloses preparation of diphenylalkylamines having effect on the heart and circulation.

SUMMARY OF THE INVENTION

In accordance with the present invention, novel therapeutically active diarylpropylamines have been found which like the 3,3-diphenylpropylamines known from WO 89/06644 and WO 94/11337 above have favourable anticholinergic properties, and which therefore also can be used for the control of events mediated by acetylcholine, like urination.

In one aspect, the present invention provides novel compounds represented by the general formula I:

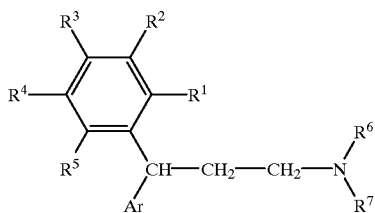

I wherein:
$R^1$ is hydrogen, hydroxy, alkyl, alkoxy, hydroxyalkyl, trifluoromethyl, amino, alkylcarbonylamino, alkylcarbonyloxy, halogen,
$R^2$ and $R^3$ independently are hydrogen, hydroxy, alkyl, alkoxy, hydroxyalkyl, halogen, alkoxycarbonylalkyl, carbamoyl, sulphamoyl,
$R^4$ is ω-hydroxyalkoxy, ω-aminoalkoxy, ω-aminoalkylamino, alkoxyalkyl, hydroxyalkoxyalkylaminoalkyl, dihydroxyalkyl, formyl, alkylcarbonyl, alkoxycarbonyl, alkoxycarbonylalkyl, alkylcarbonylaminoalkyl, aminoalkyl, alkylaminoalkyl, dialkylaminoalkyl, carboxyalkyl, carbamoylalkyl, carboxamidoalkyl, carboxyl, amino, nitro, cyano, nitrilo, cyanoalkyl, azido, alkyl of at least two carbon atoms, alkoxy of at least two carbon atoms, hydroxyalkyl of at least two carbon atoms,
$R^5$ is hydrogen, halogen, alkyl,
Ar is aryl or heteroaryl which may be mono- or independently disubstituted by alkyl, alkoxy, hydroxy, hydroxyalkyl, halogen, alkoxycarbonylalkyl, carbamoyl, sulphamoyl, and
$R^6$ and $R^7$ are hydrocarbyl groups which may be the same or different, together containing at least three carbon atoms, and which may carry one or more hydroxy groups, and wherein carbon atoms may be interconnected by oxygen atoms, and wherein $R^6$ and $R^7$ may form a ring together with the amine nitrogen,
with the provisos that (a) when:
  (i) at least two of $R^2$, $R^3$ and $R^5$ are other than hydrogen, or
  (ii) $R^1$ is other than hydroxy or methoxy, and Ar is other than phenyl that is ortho-substituted by hydroxy or methoxy, or
  (iii) Ar is heteroaryl, or
  (iv) at least one of $R^6$ and $R^7$ is aromatic hydrocarbyl or cycloalkyl, then
$R^4$ may also be hydrogen, methyl, methoxy, hydroxy, hydroxymethyl, halogen, carbamoyl, sulphamoyl;
and (b), when Ar is unsubstituted phenyl, then $R^1$, $R^2$, $R^3$, $R^4$ and $R^5$ can not all be hydrogen;
their salts with physiologically acceptable acids and, when the compounds can be in the form of optical isomers, the racemic mixture and the individual enantiomers.

In another aspect, the present invention provides the compounds having the general Formula I above for therapeutical use, especially for the treatment of urinary incontinence related disorders.

In still another aspect, the present invention provides a pharmaceutical composition comprising one or more compounds of the general Formula I above as the active ingredient, preferably together with a pharmaceutically acceptable carrier and, if desired, other pharmacologically active agents.

In yet another aspect, the present invention provides a method of treating a patient (animals, including humans) suffering from a disorder related to urinary incontinence, which method comprises the step of administering to the said patient an effective amount of a compound having the general Formula I above.

In another aspect, the present invention provides the compounds according to Formula I for use as a pharmaceutically active substance, especially as an anticholinergic agent.

In yet another aspect, the present invention provides the use of the compounds having the general Formula I above for the manufacture of a medicament for the treatment of urinary incontinence related disorders.

In still another aspect, the present invention provides processes for preparing compounds having the general Formula I above.

DETAILED DESCRIPTION OF THE INVENTION

The present invention comprises novel 3,3-diarylpropylamines and their pharmaceutically acceptable salts which are characterized by Formula I above and which are useful as anticholinergic agents. The compounds are particularly useful for treatment of urinary incontinence.

One subgroup of compounds of Formula I is defined by the substituent $R^4$ being ω-hydroxyalkoxy, ω-aminoalkoxy, ω-aminoalkylamino, alkoxyalkyl, hydroxyalkoxyalkyl-aminoalkyl, dihydroxyalkyl, formyl, alkylcarbonyl, alkoxycarbonyl, alkoxycarbonylalkyl, alkylcarbonyl-aminoalkyl, aminoalkyl, alkylaminoalkyl, dialkylaminoalkyl, carboxyalkyl, carbamoylalkyl, carboxamidoalkyl, carboxyl, amino, nitro, cyano, nitrilo, cyanoalkyl, or azido.

In a limited group of compounds within this subgroup, $R^1$ is hydrogen or methyl, $R^2$, $R^3$ and $R^5$ are either all hydrogen or one of $R^2$, $R^3$ and $R^5$ is methyl, methoxy, hydroxy, carbamoyl, sulphamoyl or halogen, and the others are hydrogen, and Ar is phenyl or phenyl which is mono- or independently disubstituted by methyl, methoxy, hydroxy, hydroxymethyl, carbamoyl, sulphamoyl or halogen.

Another subgroup of the compounds of Formula I is defined by Ar being heteroaryl.

In a limited group of compounds within this subgroup, $R^1$ is hydrogen or methyl, and $R^2$, $R^3$, $R^4$ and $R^5$ are either all hydrogen or one of $R^2$, $R^3$, $R^4$ and $R^5$ is methyl, methoxy, hydroxy, hydroxymethyl, carbamoyl, sulphamoyl or halogen, and the others are hydrogen.

Still another subgroup of the compounds of Formula I is defined by $R^1$ being hydrogen, alkyl, hydroxyalkyl, trifluoromethyl, amino, alkylcarbonylamino, alkylcarbonyloxy, or halogen. Preferaby, Ar is then other than phenyl that is ortho-substituted by hydroxy or alkoxy.

In a limited group of compounds within this subgroup, $R^1$ is hydrogen or methyl, $R^2$, $R^3$, $R^4$ and $R^5$ are either all hydrogen or one of $R^2$, $R^3$, $R^4$ and $R^5$ is methyl, methoxy, hydroxy, hydroxymethyl, carbamoyl, sulphamoyl or halogen, and the others are hydrogen, and Ar is phenyl or phenyl which is mono- or independently disubstituted by methyl, methoxy, hydroxy, hydroxymethyl, carbamoyl, sulphamoyl or halogen.

Yet another subgroup of the compounds of Formula I is defined by at least one of $R^6$ and $R^7$ being aromatic hydrocarbyl, cycloalkyl or a hydrocarbyl chain wherein carbon atoms are interconnected by an oxygen atom at one or more positions.

In a limited group of compounds within this subgroup, $R^1$ is hydrogen or methyl, $R^2$, $R^3$, $R^4$ and $R^5$ are either all hydrogen or one of $R^2$, $R^3$, $R^4$ and $R^5$ is methyl, methoxy, hydroxy, hydroxymethyl, carbamoyl, sulphamoyl or halogen, and the others are hydrogen, and Ar is phenyl or phenyl which is mono- or independently disubstituted by methyl, methoxy, hydroxy, hydroxymethyl, carbamoyl, sulphamoyl or halogen.

In the compounds of Formula I, "alkylo", separately and in combinations, is preferably $C_{1-8}$alkyl, i.e. methyl, ethyl, propyl, butyl, pentyl, hexyl, heptyl, octyl, and isomeric forms thereof, more preferably $C_{1-6}$alkyl, especially $C_{1-4}$alkyl.

Similarly, "alkoxy", separately and in combinations, is preferably $C_{1-8}$alkoxy, i.e. methoxy, ethoxy, propoxy, butoxy, pentoxy, hexoxy, heptoxy, octoxy, and isomeric forms thereof, more preferably $C_{1-6}$alkoxy, especially $C_{1-4}$alkoxy.

"Aryl" means phenyl or naphthyl. "Heteroaryl" refers to a 5- or 6-membered heteroaromatic ring having from one to three heteroatoms, and which optionally may be fused to a homoaromatic ring, such as a benzene ring. Exemplary heteroaryl groups are morpholinyl, thienyl, furyl, piperazinyl, piperidinyl, imidazolinyl, pyridazolinyl, oxazolyl, isoxazolyl, pyrrolyl, imidazolyl, pyrazolyl, pyridyl, pyrazinyl, pyrimidinyl or pyridazinyl.

"Halogen" includes fluoro, chloro, bromo and iodo.

When aryl is mono-substituted, it is preferably substituted in 2-position. When aryl is di-substituted, it 35 is preferably substitued in positions 2 and 4. Preferred substituents are methyl, methoxy, hydroxy, hydroxymethyl, halogen, alkoxycarbonylalkyl, carbamoyl, sulphamoyl, especially methyl, hydroxymethyl and halogen. Aryl is preferably phenyl.

Preferred heteroaryl groups are thienyl, pyrryl, thiazolyl, oxazolyl, methylthiazolyl and methylpyrryl.

$R^1$ is preferably hydroxy, halogen, trifluoromethyl, amino, methoxy or hydroxymethyl.

$R^2$ and $R^3$ are preferably selected from hydrogen, hydroxy and methoxy.

$R^4$ is preferably hydrogen, formyl, alkoxycarbonyl, alkylcarbonyl, hydroxyalkyl, alkoxyalkyl, carboxamidoalkyl, carbamoylalkyl, aminoalkyl, amino, azido, cyanoalkyl, carboxy or carboxyalkyl. More preferably, $R^4$ is hydrogen, formyl, hydroxymethyl, hydroxyethyl, hydroxypropyl, hydroxybutyl, hydroxypentyl, hydroxyhexyl, ethoxymethyl, methoxycarbonyl, amino, aminopropyl, acetyl, 1,2-hydroxyethyl, ethylaminomethyl, or hydroxyethoxyethyl-aminoethyl.

$R^5$ is preferably hydrogen.

$R^6$ and $R^7$ independently of each other preferably signify a saturated hydrocarbyl group, especially a saturated aliphatic hydrocarbyl group, such as $C_{1-8}$-alkyl, especially $C_{1-6}$-alkyl, or adamantyl, $R^6$ and $R^7$ together containing at least three, preferably at least four carbon atoms. $R^6$ and $R^7$ may carry one or more hydroxy groups and they may be joined to form a ring together with the nitrogen atom. It is preferred that at least one of $R^6$ and $R^7$ comprises a branched carbon chain.

Exemplary groups $-NR^6$, $R^7$ are diethylamino, diisopropylamino, methyl-tert.-butylamino, methyl-tert.-pentylamino, piperidino, 2,2,6,6-tetramethylpiperidino, methylcyclobutylamino, methylcyclopentylamino, methylcyclohexylamino, methylcycloheptylamino, pyrrolidino, 2,2,5,5-tetramethylpyrrolidino, N-methyl-N-adamantylamino, especially diisopropylamino.

Representative compounds of Formula I are:

N,N-diisopropyl-3-(2-fluorophenyl)-3-phenylpropanamine hydrochloride

N,N-diisopropyl-3-(5-formyl-2-hydroxy-phenyl)-3-phenylpropanamine, and its (R)-isomer N,N-diisopropyl-3-(2-hydroxy-5-methyloxycarbonylphenyl)-3-phenylpropanamine, and its (R)-isomer N,N-diisopropyl-3-(5-acetyl-2-hydroxyphenyl)-3-phenylpropanamine, and its (R)-isomer N,N-diisopropyl-3-[2-hydroxy-5-(2-hydroxyethyl)phenyl]-3-phenylpropanamine, and its (R)-isomer N,N-diisopropyl-3-[2-hydroxy-5-(1-hydroxyethyl)phenyl]-3-phenylpropanamine, and its 3(R)-isomer N,N-diisopropyl-3(R)-8 5-(1(R*),2-dihydroxyethyl)-2-hydroxyphenyl]-3-phenylpropanamine, and its 1(S*)-isomer N,N-diisopropyl-3-[2-hydroxy-5-(6-hydroxyhexyl)phenyl]-3-phenylpropanamine, and its (R)-isomer N,N-diisopropyl-3-(5-ethoxymethyl-2-hydroxyphenyl)-3-phenylpropanamine, and its (R)-isomer N,N-diisopropyl-3-[5-(3-aminopropyl)-2-hydroxyphenyl]-3-phenylpropanamine, and its (R)-isomer N,N-diisopropyl-3-[5-(3-acetamidopropyl)-2-hydroxyphenyl]-3-phenylpropanamine, and its (R)-isomer N,N-diisopropyl-3-[5-(2-cyanoethyl)-2-hydroxyphenyl]-3-phenylpropanamine, and its (R)-isomer N,N-diisopropyl-3-5-amino-2-hydroxyphenyl)-3-phenylpropanamine, and its (R)-isomer N,N-diisopropyl-3-(5-azido-2-hydroxyphenyl)-3-phenylpropanamine, and its (R)-isomer N,N-diisopropyl-3-[2-hydroxy-5-(3-hydroxypropyl)phenyl]-3-phenylpropanamine, and its (R)-isomer N-cyclobutyl-N-methyl-3-(2-hydroxyphenyl)-3-phenylpropanamine N,N-diisopropyl-3-(2-hydroxyphenyl)-3-(2-thienyl)propanamine N,N-diisopropyl-3-(2-hydroxy-5-methylphenyl)-3-(2-thienyl)propanamine, and its (R)-isomer The compounds of Formula I may, in accordance with the present invention, be prepared by per se conventional methods, and especially by a) reacting a compound of Formula II

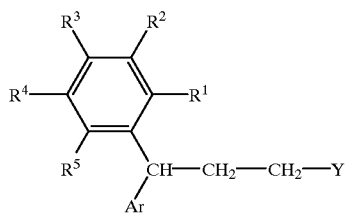

II wherein $R^1$ to $R^5$ and Ar are as defined above for Formula I, and Y is a leaving group, with an amine $HNR^6,R^7$, wherein $R^6$ and $R^7$ are as defined above, or b) reducing a compound of Formula III

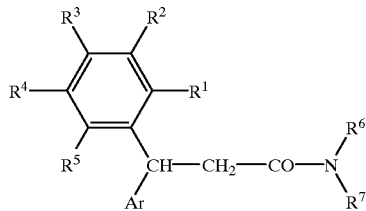

III wherein $R^1$ to $R^7$ and Ar are as defined above for Formula I and any hydroxy groups may be protected, or c) N-alkylating a secondary amine of Formula IV

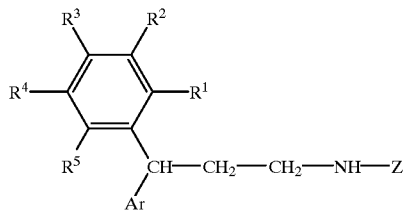

IV wherein $R^1$ to $R^5$ and Ar are as defined above for Formula I and any hydroxy groups may be protected, and wherein Z has the same meaning as $R^6$ and $R^7$, or d) reducing a compound of Formula Va or Vb

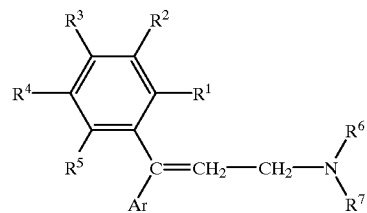

Va

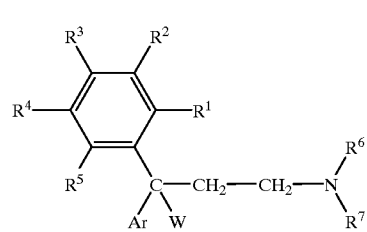

Vb wherein $R^1$ to $R^7$ and Ar are as defined above for Formula I and any hydroxy groups may be protected, and W signifies a hydroxy group or halogen, or e) in a compound of Formula VI

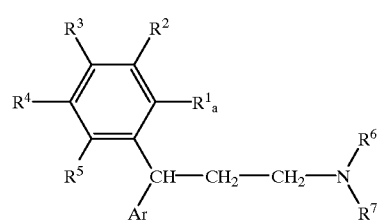

VI wherein $R^2$ to $R^7$ and Ar are as defined above for Formula I, and $R^1a$ is carboxyl or alkoxy, converting $R^1a$ to hydroxy, or f) in a compound of Formula VII

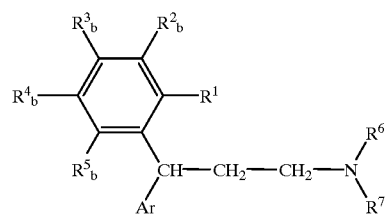

VII wherein $R^1$, $R^6$, $R^7$ and Ar are as defined above for Formula I, and one of $R^2b$ to $R^5b$ is alkylene and the others are as defined above for $R^2$ to $R^5$, reducing alkylene to alkyl, hydroxyalkyl or dihydroxyalkyl, or g) in a compound of Formula I as defined above, converting one or more of groups $R^1$ to $R^5$ to another or other groups $R^1$ to $R^5$, or h) reacting a compound of Formula VIII

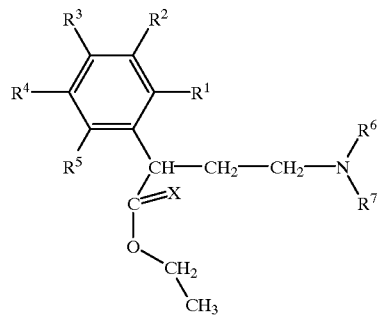

wherein $R^1$ to $R^7$ are as defined above for Formula I, and X is oxygen or sulphur, with a compound of Formula IX

to form a compound of Formula Ia

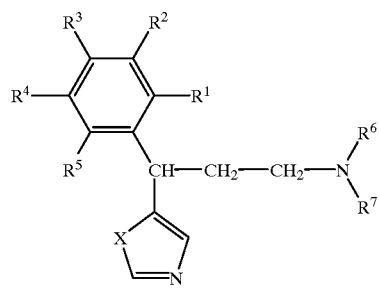

wherein $R^1$ to $R^7$ and X are as defined above, or i) reacting a compound of Formula VIII above, wherein X is oxygen, with a compound of Formula X

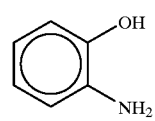

to form a compound of Formula Ib

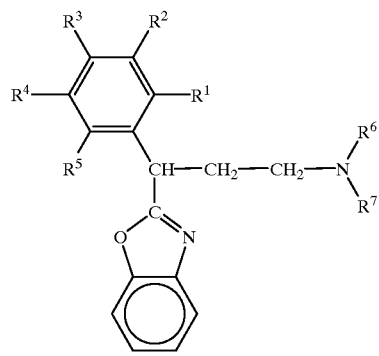

wherein $R^1$ to $R^7$ are as defined above for Formula I, or j) converting a compound of Formula XI

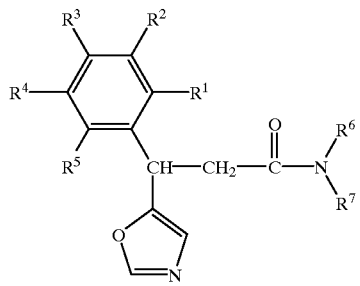

wherein $R^1$ to $R^7$ are as defined above for Formula I, to a compound of Formula XII

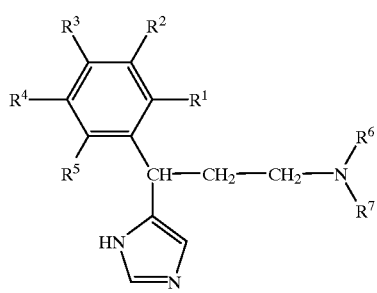

wherein $R^1$ to $R^7$ are as defined above for Formula I, or k) converting a compound of Formula XIII

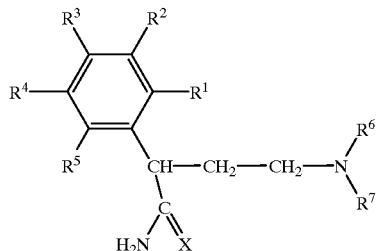

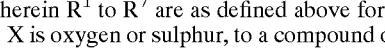

wherein $R^1$ to $R^7$ are as defined above for Formula I, and X is oxygen or sulphur, to a compound of Formula XIV

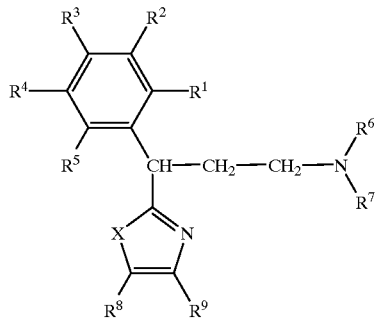

wherein $R^1$ to $R^7$ and X are as defined above for Formula I, and $R^8$ and $R^9$ independently are hydrogen or alkyl, and i) when necessary splitting off hydroxy protecting groups in the compounds obtained, ii) if desired converting the obtained bases of Formula I into salts thereof with physiologically acceptable acids, or vice versa, and/or iii) if desired separating an obtained mixture of optical isomers into the individual enantiomers.

Appropriate reaction conditions in the above reactions may readily be selected by the skilled person with reference to analogous prior art methods and with due consideration of the specific Examples below. The necessary starting materials are either known or may be prepared in analogy with the preparation of known compounds.

The separation of mixtures of optical isomers, according to ii) above, into the individual enantiomers can e.g. be achieved by fractional crystallisation of salts with chiral acids or by chromatographic separation on chiral columns.

In accordance with the present invention, the compounds of Formula I, in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of Formula I in association with compatible pharmaceutically acceptable carrier materials, or diluents, as is well known in the art. The carriers may be any inert material, organic or inorganic, suitable for enteral, percutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, and conventional additives, such as stabilizers, wetting agents, emulsifiers, flavouring agents, buffers, and the like.

The compositions according to the invention can e.g. be made up in solid or liquid form for oral administration, such as tablets, capsules, powders, syrups, elixirs and the like, in the form of sterile solutions, suspensions or emulsions for parenteral administration, and the like.

The compounds and compositions can, as mentioned above, be used for the same therapeutical indications as the compounds of the above-mentioned Wo 89/06644 or WO 94/11337, i.e. for the treatment of acetylcholine-mediated disorders, such as urinary incontinence, especially urge incontinence. The dosage of the specific compound will vary depending on its potency, the mode of administration, the age and weight of the patient and the severity of the condition to be treated. The daily dosage may, for example, range from about 0.01 mg to about 4 mg per kilo of body weight, administered singly or multiply in doses e.g. from about 0,05 mg to about 200 mg each.

The invention will be further illustrated by the following non-limiting example and pharmacological tests.

General

N.M.R data were acquired on a Jeol JNM-EX 270 or a Varian Unity 500 spectrometer. Spectra were recorded with tetramethylsilane (TMS) as internal standard at 30° C. Infrared spectra were recorded on a Perkin-Elmer Model Model 841 spectrophotometer. Non-corrected melting points were obtained on a Koeffler apparatus. Gas chromatography was performed on a HP 5940 instrument with a 10 m HP-1 column and the oven heated in the linear temperature gradient mode. All lithium aluminum hydride reductions were quenched by the use of the procedure according to V. Micovic and M. Mihailovic (J. Org. Chem. 18, 1190 (1953)).

EXAMPLE 1

N-(5-Hydroxy-3-oxapentyl)-N-isopropyl-3-(2-hydroxy-5-methylphenyl)-3-phenylpropanamine hydrochloride A solution of N-(5-hydroxy-3-oxapentyl)-N-isopropyl-3-(2-hydroxy-5-methylphenyl)-3-phenylpropanamide (2.75 g, 7 mmol) in THF (40 mL) was added to lithium aluminum hydride (LAH) (0.50 g, 13 mmol) and the mixture was stirred at ambient temperature for 2 h. The reaction was quenched and the solvent evaporated. The residue was chromatographed on silica (toluene-triethylamine 19:1). The title compound was crystallised by dissolving the free amine in diethyl ether and adding hydrogen chloride in diethyl ether. Yield 0.75 g (27%); mp 70–75° C. $^1$H NMR (DMSO-d6) δ1.17 (q, 3H), 1.23 (t, 3H), 2.18 (d, 3H), 2.47 (m, 2H), 2.84–3.07 (m, 2H), 3.15 (m, 1H), 3.37 (m, 1H), 3.42 (d, 2H), 3.46 (s, 2H), 3.67 (m, 1H), 3.74 (m, 2H), 4.30 (m, 1H), 4.76 (br, 1H), 6.71 (d, 1H), 6.80 (d, 1H), 7.06 (d, 1H), 7.16 (t, 1H), 7.27 (t, 2H), 7.33 (d, 2H), 9.29 (d, 1H) and 10.07 (br, 1H). Anal. ($C_{23}H_{33}NO_3$HCl) C, H, N.

The starting compound N-(5-hydroxy-3-oxapentyl)-N-isopropyl-3-(2-hydroxy-5-methylphenyl)-3-phenylpropanamide was prepared as follows:

1.1 Trans-3-(2-benzyloxy-5-methylphenyl)-3-phenylpropenoic acid

A solution of triethyl phosphonoacetate (22.4 g, 0.10 mol) in THF (150 mL) was added to sodium hydride (80%, 2.7 g, 0.09 mol) under nitrogen during 15 min. The resulting mixture was refluxed for 15 min whereafter a solution of 2-benzyloxy-5-methyl-benzophenone (15.1 g, 0.05 mol) in THF (50 mL) was added. The reaction mixture was refluxed for 19 h. Water and sodium hydroxide (10 g, 0.25 mol) were added and most of the THF was distilled off. Ethanol was added until a clear solution was obtained and the reflux was continued for a few minutes. Water was added to a total volume of 1 L and the mixture was washed with diethyl ether. Hydrochloric acid was added to the water-phase and a crystalline mass was obtained. The pure trans-isomer was obtained by recrystallisation from ethanol. Yield 10.4 g (60%). $^1$H NMR (DMSO-d6) δ2.24 (s, 3H), 4.92 (s, 2H), 6.41 (s, 1H), 6.87 (d, 1H), 6.98 (d, 1H), 7.03 (m, 2H) 7.12 (m, 1H), 7.22 (m, 3H), 7.29 (m, 1H), 7.30 (m, 1H) and 7.33–7.39 (m, 3H).

1.2 trans-N-(5-Hydroxy-3-oxapentyl)-N-isopropyl-3-(2-benzyloxy-5-methylphenyl)-3-phenylpropenamide A solution of DCC (5.2 g, 17 mmol) in THF (20 mL) was added to a solution of trans-3-(2-benzyloxy-5-methylphenyl)-3-phenylpropenoic acid (6.9 g, 20 mmol), 2-(2-isopropylaminoethoxy)-ethanol, triethylamine (2.5 g, 25 mmol) and hydroxysuccinimide (2.8 g, 24 mmol) in THF (50 mL). The reaction mixture was stirred for 20 h. The solvent was evaporated and the residue chromatographed on silica (gradient from toluene to ethyl acetate). Yield 5.9 g (62%).

1.3 trans-N-(5-Hydroxy-3-oxapentyl)-N-isopropyl-3-(2-hydroxy-5-methylphenyl)-3-phenylpropanamide A solution of trans-N-(5-hydroxy-3-oxapentyl)-N-isopropyl-3-(2-benzyloxy-5-methylphenyl)-3- phenylpropenamide (5.9 g, 12 mmol) in acetic acid (50 mL) was hydrogenatated over Pd/C (10%, 0.5 g) for 16 h. Filtering and evaporation of solvent left a residue that was chromatographed on silica (ethyl acetate). Yield 2.83 g (61%).

EXAMPLE 2

N-Cycloheptyl-N-methyl-3-(2-hydroxy-5-methylphenyl)-3-phenylpropanamine hydrochloride A solution of N-cycloheptyl-N-methyl-3-(2-hydroxy-5-methylphenyl)-3-phenylpropanamide (0.93 g, 2.5 mmol) in THF (20 mL) was added to LAH (0.22 g, 5.6 mmol) and the mixture was stirred at reflux temperature for 30 min. The reaction was quenched and the solvent evaporated. The residue was chromatographed on silica (chloroform-methanol 9:1). The amine salt was obtained by dissolving the free amine in diethyl ether and adding hydrogen chloride in diethyl ether. Yield 0.45 g (46%); mp. 230–232° C. $^1$H NMR (DMSO-d6) δ1.27–1.70 (m, 10H), 1.88 (br, 1H), 2.05 (d, 1H), 2.17 (s, 3H), 2.42 (br, 1H), 2.60 (s, 3H), 2.85 (br, 2H), 3.34 (m, 1H), 4.30 (t, 1H), 6.72 (d, 1H), 6.80 (dd, 1H), 7.05 (br, 1H), 7.15 (t, 1H), 7.27 (t, 2H), 7.31 (d, 2H), 9.31 (s, 1H) and 10.53 (br, 1H). Anal. ($C_{24}H_{33}NO·HCl$) C, H, N.

The starting compound N-cycloheptyl-N-methyl-3-(2-hydroxy-5-methylphenyl)-3-phenylpropanamide was prepared as follows:

2.1 N-Cycloheptyl-trans-3-(2-benzyloxy-5-methylphenyl)-3-phenylpropenamide

A solution of DCC (5.2 g, 25 mmol) in THF (50 mL) was added to a solution of trans-3-(2-benzyloxy-5-methylphenyl)-3-phenylpropenoic acid (Example 1.1), (6.9 g, 20 mmol), cycloheptylamine (2.6 g, 23 mmol), triethylamine (2.0 g, 20 mmol) and hydroxysuccinimide (2.4 g, 21 mmol) in THF (50 mL). The reaction mixture was stirred for 1 h at room temperature. Another portion of cycloheptylamine (1.3 g) was added and the reaction mixture was left stirring for another 1 h. The mixture was filtered and the filtrate evaporated. The residue was dissolved in diethyl ether and washed with hydrochloric acid (1M), water and brine in subsequent order. After evaporation of the solvent, the residue was crystallised from toluene-hexane to give 7.3 g (83%). $^1$H NMR (CDCl$_3$) δ1.06 (br, 2H), 1.25–1.74 (m, 10H), 2.30 (s, 3H), 3.83 (m, 1H), 4.95 (s, 2H), 5.50 (d, 1H), 6.49 (s, 1H), 6.90–7.08 (m, 4H), and 7.12–7.44 (m, 9H).

2.2 N-Cycloheptyl-N-methyl-trans-3-(2-benzyloxy-5-methylphenyl)-3-phenylpropenamide A solution of N-cycloheptyl-trans-3-(2-benzyloxy-5-methylphenyl)-3-phenylpropenamide (4.4 g, 10 mmol) and methyliodide (4 g, 30 mmol) in DMF (10 mL) was added to sodiumhydride (80%, 1.2 g, 40 mmol) at ambient temperature and the mixture was stirred for 60 min. Excess sodium hydride was destroyed by adding methanol, and the reaction mixture was then partioned between toluene and water. The organic layer was dried (MgSO$_4$) and the solvent was evaporated. The residue was crystallised from toluene-hexane to yield 4.4 g (97%). $^1$H NMR (CDCl$_3$) (almost 1:1 mixture of rotameres) δ1.20–1.80 (m, 12H), 2.30 (m, 3H) 2.61 (s, 1.5H), 2.71 (s, 1.5H), 3.93 (m, 0.5H), 4.46 (m, 0.5H), 4.81 (m, 1H), 6.43 (m, 1H), 6.81 (m, 2H) and 7.08–7.35 (m, 10H).

2.3 N-Cycloheptyl-N-methyl-3-(2-hydroxy-5-methylphenyl)-3-phenylpropanamide A solution of N-cycloheptyl-N-methyl-trans-3-(2-benzyloxy-5-methylphenyl)-3-phenylpropenamide (3.15 g, 7 mmol) in acetic acid (40 mL) was hydrogenated over Pd/C (10%, 0.2 g) for 72 h. The reaction mixture was filtered and the solvent evaporated. The residue was chromatographed on silica (toluene-ethyl acetate 9:1). Yield 0.95 g (37%). $^1$H NMR (CDCl$_3$) δ1.26–1.98 (m, 12H), 2.02 (s, 3H), 2.12 (s, 3H), 2.28 (m, 1H), 2.52 (m, 1H), 2.71 (m, 1H), 4.36 (dd, 1H), 6.39 (s, 1H), 6.76 (s, 2H), 7.15 (m, 2H) and 7.25 (m, 5H).

EXAMPLE 3

N-Cyclohexyl-N-methyl-3-(2-hydroxy-5-methylphenyl)-3-phenylpropanamine hydrochloride A solution of N-cyclohexyl-N-methyl-trans-3-(2-benzyloxy-5-methylphenyl)-3-phenylpropenamide (4.0 g, 9 mmol) in THF (90 mL) was added to LAH (0.50 g, 13 mmol) in THF (5 mL) and the mixture was stirred at ambient temperature for 2.5 h. The reaction was quenched and the solvent evaporated. The resulting oil was hydrogenated over Pd/C (10%, 1 g) in acetic acid (70 mL) for 20 h. After filtration and evaporation of the solvent, the residue was chromatographed on silica (chloroform:methanol 99:1). The amine salt was obtained by dissolving the free amine in diethyl ether and adding hydrogen chloride in diethyl ether. Yield 1.2 g (36%); mp. 179–183° C. $^1$H NMR (DMSO-d6) δ1.05 (m, 1H), 1.21–1.38 (m, 4H), 1.51 (d, 1H), 1.74 (br, 2H), 1.86 (br, 1H), 2.00 (d, 1H), 2.17 and 2.19 (s, 3H), 2.39–2.56 (m, 2H), 2.63 (m, 3H), 2.82 (m, 1H), 2.93 (m, 1H), 3.17 (m, 1H), 4.32 (q, 1H), 6.73 and 6.75 (d, 1H), 6.79 and 6.81 (t, 1H), 7.02 and 7.10 (d, 1H), 7.14–7.18 (m, 1H), 7.25–7.29 (m, 2H), 7.33 (t, 2H), 9.34 (br, 1H) and 10.78 (s, 1H). Anal. ($C_{23}H_{31}NO·HCl$) C, H, N.

The starting compound N-cyclohexyl-N-methyl-trans-3-(2-benzyloxy-5-methylphenyl)-3-phenylpropenamide was prepared as follows:

3.1 N-Cyclohexyl-N-methyl-trans-3-(2-benzyloxy-5-methylphenyl)-3-phenylpropenamide A solution of DCC (5.2 g, 25 mmol) in THF (50 mL) was added to a solution of trans-3-(2-benzyloxy-5-methylphenyl)-3-phenylpropenoic acid (Example 1.1), (6.9 g, 20 mmol), N-methyl-cyclohexylamine (2.6 g, 23 mmol), triethylamine (2.0 g, 20 mmol) and hydroxysuccinimide (2.4 g, 21 mmol) in THF (50 mL). The reaction mixture was stirred for 2 h. A second portion of DCC (2.5 g, 13 mmol) and N-methyl-cyclohexylamine (1.5 g, 13 mmol) was added and the reaction mixture was left stirring for 16 h. Diethyl ether and hydrochloric acid (1M) were added and the organic phase was washed with brine. The organic layer was evaporated and the residue was chromatographed on silica (toluene-ethyl acetate 9:1). Yield 5.5 g (63%). $^1$H NMR (DMSO-d6) (almost 1:1 mixture of rotameres) δ0.88–1.06 (m, 2H), 1.16–1.39 (m, 5H), 1.55 (t, 2H), 1.67 (br, 1H), 2.21 (s, 1.5H), 2.23 (s, 1.5H) 2.56 (s, 1.5H), 2.67 (s, 1.5H), 3.67 (m, 0.5H), 4.05 (m, 0.5H), 4.82 (s, 1H), 4.85 (s, 1H), 6.57 (s, 0.5H), 6.59 (s, 0.5H), 6.84 (dd, 1H), 6.87 (d, 0.5H), 6.89 (t, 1H), 6.95 (dd, 1H), 6.98 (d, 0.5H), 7.12 (dd, 1H), 7.17 (m, 3H), 7.27 (m, 2H), and 7.32 (m, 3H).

EXAMPLE 4

N,N-Diisopropyl-3-(2-trifluoromethylphenyl)-3-phenylpropanamine hydrochloride Boran.SMe$_2$-complex in THF (7 mL, 14 mmol) was gently refluxed with a weak stream of nitrogen for 30 minutes. N,N-Diisopropyl-3-(2-trifluoromethylphenyl)-3- phenylpropanamide (1.55 g, 4.2 mmol) was added to the refluxing solution and the reflux was continued for 1 h. The reaction mixture was partioned between diethyl ether and sodium hydroxide (1M). The solvent of organic layer was evaporated and the residue was chromatographed on silica (toluene-triethylamine 9:1) to yield the free amine. The hydrochloride salt was obtained by dissolving the amine in diethyl ether with the addition of hydrogen chloride in diethyl ether. The resulting oil produced crystals after some time stirring in diethyl ether. Yield 0.39 g (23%); mp. 143–144° C. $^1$H NMR (DMSO-d6) δ1.19 (q, 6H), 1.25 (dd, 6H), 2.53 (m, 1H), 2.70 (m, 1H), 2.87 (m, 2H), 3.59 (m, 2H), 4.38 (t, 1H), 7.24 (t, 1H), 7.35 (t, 2H), 7.39 (d, 2H), 7,45 (t, 1H), 7.68 (t, 1H), 7.74 (t, 2H) and 10.25 (br, 1H). Anal. ($C_{22}H_{28}NF_3$.HCl) C, H, N.

The starting compound N,N-diisopropyl-3-(2-trifluoromethylphenyl)-3-phenylpropanamide was prepared as follows:

4.1 Diethyl N,N-diisopropylacetamide phosphonate

A mixture of triethylphosphite (23 g, 0.14 mol) and N,N-diisopropyl 2-bromoacetamide (29 g, 0.13 mol) was heated to 110° C. for 3 h to yield 35 g (97%). The product was used without purification.

4.2 N,N-Diisopropyl-3-(2-trifluoromethylphenyl)-3-phenylpropenamide

A solution of diethyl N,N-diisopropylacetamide phosphonate (8.4 g, 30 mmol) in THF (20 mL) was added dropwise to sodium hydride (80%, 0.85 g, 29 mmol) during 30 min, keeping the temperature below 30° C. A solution of 2-trifluoromethyl-benzophenone (5.0 g, 20 mmol) in THF (20 mL) was added and the reaction mixture was heated to 50° C. and kept at that temperature for 16 h. A second portion of the phosphorous ylide (15 mmol), prepared as above, was added. After another 24 h at 50° C. the mixture was partioned between diethyl ether and water. The etheral layer was evaporated and the residue chromatographed on silica (toluene-ethyl acetate 9:1) yielding 3.0 g (41%) as a mixture of the E- and Z-isomers. Labels a and b refer to the different isomers. $^1$H NMR (CDCl$_3$-d) δ0.80 (d, 6Ha), 1.08 (d, 3Hb), 1.24 (t, 6Hb), 1.31 (d, 3Hb), 1.44 (d, 6Ha), 3.32 (m, 1Ha), 3.34 (m, 1Hb), 4.19 (m, 1Hb), 4.32 (m, 1Ha), 6.04 (s, 1Ha), 6.65 (s, 1Hb) and 7.18–7.75 (m, 9Ha, 9Hb).

4.3 N,N-Diisopropyl-3-(2-trifluoromethylphenyl)-3-phenylpropanamide

A solution of N,N-diisopropyl-3-(2-trifluoromethylphenyl)-3-phenylpropenamide (2.95 g, 8.1 mmol) in ethanol (50 mL) was hydrogenated over Pd/C (10%, 300 mg) at normal pressure for 24 h. The catalyst was filtered off, the solvent partly evaporated and the product collected after crystallisation. Yield 1.78 g (60%). $^1$H NMR (CDCl$_3$-d) δ1.16 (m, 6H), 1.30 (m, 6H), 2.86 (dd, 1H), 3.11 (dd, 1H), 3.41 (m, 1H), 4.03 (m, 1H), 5.12 (m,1H) and 7.10–7.78 (m, 9H).

EXAMPLE 5

N,N-Diisopropyl-3-(2-hydroxyphenyl)-3-(3-pyridyl)-propanamine dihydrochloride A solution of N,N-diisopropyl-3-(2-methoxyphenyl)-3-(3-pyridyl)-propanamide (2.8 g, 8 mmol) in THF (25 mL) was added to LAH (1.3 g, 32 mmol). The reaction mixture was refluxed for 4 h whereafter the reaction was quenched and the solvent evaporated. The residue was chromatographed on silica (toluene-triethylamine 99:1) to give 2.2 g. The product (1.3 g, 4 mmol) was dissolved in dichloromethane (20 mL) and the solution was cooled to −78° C. and boron tribromide (1 g, 8 mmol) was added dropwise and the reaction mixture was allowed to reach room temperature during 1 h. The reaction mixture was washed with sodium hydroxide (1M) and brine and the organic phase was dried (MgSO$_4$) and the solvent evaporated. The residue was chromatographed on silica (toluene-triethylamine 9:1) to give 0.35 g. The free amine was dissolved in diethyl ether and hydrogen chloride in diethyl ether was added to produce the dihydrochloride as crystals which soon rearranged to a hard glass. $^1$H NMR (DMSO-d6) δ1.22 (dd, 6H), 1.28 (dd, 6H), 2.60 (m,1H), 2.70 (m, 1H), 2.93 (m, 2H), 3.60 (m, 2H), 4.60 (t, 1H), 6.85 (t, 1H), 6.89 (d, 1), 7.11 (t, 1H), 7.38 (d, 1H), 7.96 (dd, 1H), 8.46 (d, 1H), 8.75 (d, 1H), 8.85 (s, 1H), 9.90 (br, 1H) and 10.14 (s, 1H).

The starting compound N,N-diisopropyl-3-(2-methoxyphenyl)-3-(3-pyridyl)-propanamide was prepared as follows:

5.1 2-Methoxyphenyl-3-pyridyl-ketone

A solution of 2-bromoanisole (21 g, 0.11 mol) in diethyl ether (100 mL) was added to magnesium turnings during 45 minutes with heating. After the addition the reflux was continued for 15 min. The Grignard reagent was cooled to 0° C. and a solution of 3-cyanopyridine (10 g, 0.10 mol) in diethyl ether (100 mL) was added dropwise. The mixture was refluxed for a few minutes. Hydrochloric acid (20 mL, 0.24 mol, conc.) and 2-propanol (20 mL) were added and the reflux was continued for 30 min. Water and diethyl ether were added and the phases separated. The water-phase was made alkaline (2M NaOH) and was extracted with diethyl ether. The combined organic phases were dried (MgSO$_4$) and evaporated to yield 17 g. The crude was chromatographed on silica (toluene-ethyl acetate 19:1) to give 3.75 g (19%). $^1$H NMR (CDCl$_3$-d) δ3.76 (s, 3H), 7.01 (d, 1H), 7.10 (t, 1H), 7.41 (dd, 1H), 7.46 (dd, 1H), 4.53 (m, 1H), 8.12 (d, 1H), 8.75 (s, 1H) and 8.94 (s,

5.2 N,N-Diisopropyl-3-(2-methoxyphenyl)-3-(3-pyridyl)-propanamide

A solution of of diethyl N,N-diisopropylacetamide phosphonate (Example 4.1), (9.3 g, 33 mmol) in THF (40 mL) was added dropwise to sodium hydride (80%, 1.0 g, 33 mmol) during 15 min. The mixture was heated to 40° C. for 15 minutes and then cooled to 5° C. whereafter a solution of 2-methoxyphenyl-3-pyridyl-ketone (4.5 g, 21 mmol) in THF (10 mL) was added dropwise. The reaction mixture was allowed to reach room temperature and was stirred for 16 h. The reaction mixture was partioned between diethyl ether and water and the organic phase was dried (MgSO$_4$) and evaporated to yield 7.1 g of solid material. The product was hydrogenated over Pd/C (10%, 0.2 g) in acetic acid (50 mL) for 48 h. The reaction mixture was filtered and the solvent evaporated. The residue was partioned between diethyl ether and hydrochloric acid (1 M) and the phases were separated. The water-phase was made alkaline (2 M sodium hydroxide) and extracted with diethyl ether. The combined organic phases were dried (MgSO$_4$) and filtered. Crystallisation began and the mixture was diluted with hexane. Filtration gave 2.9 g (40%). $^1$H NMR (CDCl$_3$-d) δ1.14 (dd, 6H), 1.28 (d, 6H), 3.04 (dd, 2H), 3.38 (m, 1H), 3.74 (s, 3H), 4.05 (m, 1H), 5.00 (t, 1H), 6.84 (d, 1H), 6.92 (t, 1H), 7.19 (m, 3H), 7.57 (d, 1H), 8.39 (m, 1 H) and 8.55 (d, 1H). 1H).

EXAMPLE 6

N,N-Diisopropyl-3-(2-fluorophenyl)-3-phenylpropanamine hydrochloride

A solution of N,N-diisopropyl-3-(2-fluorophenyl)-3-phenylpropanamide (3.1 g, 9.4 mmol) in THF (20 mL) was added to LAH (1.0 g, 25 mmol) and the reaction mixture was stirred at reflux temperature for 2 h. More LAH (0.5 g), was added and the reflux continued for another 2 h. The reaction was quenched and the solvent evaporated. The residue was chromatographed on silica (toluene-ethyl acetate 3:1) to give 0.4 g of the free amine as a syrup. The amine was dissolved in isopropanol/diethyl ether and hydrogen chloride in diethyl ether was added to give the amine salt. Yield 0.32 g (10%); mp 152–154° C. $^1$H NMR (DMSO-d6) δ1.19 (dd, 6H), 1.26 (dd, 6H), 2.57 (m, 2H), 2.86 (m, 1H), 2.97 (m, 1H), 3.58 (m, 2H), 4.36 (t, 1H), 6.69 (dd, 1H), 7.14 (m, 1H), 7.22 (m, 2H), 7.29 (m, 1H), 7.32 (d, 2H), 7.33 (s, 2H), 7.54 (m, 1H) and 10.24 (br, 1H). Anal. ($C_{21}H_{28}NF.HCl$) H, N; C: calcd, 72.1; found, 72.6.

The starting compound N,N-diisopropyl-3-(2-fluorophenyl)-3-phenylpropanamide was prepared as follows:

6.1 trans-N,N-Diisopropyl-3-(2-fluorophenyl)-3-phenylpropenamide

A solution of diethyl N,N-diisopropylacetamide phosphonate (Example 4.1), (8.4 g, 30 mmol) in THP (20 mL) was added dropwise to sodium hydride (80%, 0.85 g, 25 mmol) during 30 min, keeping the temperature below 40° C. A solution of 2-trifluoromethyl-benzophenone (4.0 g, 20 mmol) in THF (10 mL) was added and the reaction mixture was stirred at ambient temperature for 30 min. The mixture was partioned between diethyl ether and brine. The organic layer was dried (MgSO$_4$) and evaporated to give a crystalline mass. Recrystallisation from hexane yielded 3.9 g (60%). $^1$H NMR (CDCl$_3$-d) δ0.85 (d, 6H), 1.39 (d, 6H), 3.29 (m, 1H), 4.27 (m, 1H), 6.29 (s, 1H), 7.10 (m, 3H) and 7.30 (m, 6H).

6.2 N,N-Diisopropyl-3-(2-fluorophenyl)-3-phenylpropanamide

A solution of trans-N,N-diisopropyl-3-(2-fluorophenyl)-3-phenylpropenamide (3.25 g, 10 mmol) was hydrogenated over Pd/C (10%, 300 mg) in acetic acid (30 mL) for 24 h. The catalyst was filtered off and the solvent was evaporated to yield 3.15 g (96%). $^1$H NMM (CDCl$_3$-d) δ1.12 (q, 6H), 1.28 (q, 6H), 3.05 (d, 2H), 3.38 (m, 1H), 4.03 (m, 1H), 4.93 (t, 1H) and 6.94–7.32 (m, 9H).

EXAMPLE 7

(R)-N,N-Diisopropyl-3-(5-formyl-2-hydroxyphenyl)-3-phenylpropanamine hydrochloride Hydrogen chloride in diethyl ether was added to a solution of (R)-N,N-diisopropyl-3-(5-formyl-2-hydroxyphenyl)-3-phenylpropanamine (0.81 g, 2.4 mmol) in diethyl ether and 2-propanol. Crystals were filtered to yield 0.4 g (45%); mp 178–179° C. [α]$_{Hg}$=−40° (c 1.1 in methanol). $^1$H NMR (DMSO-d6) δ1.16 (d, 3H), 1.20 (d, 3H), 1.24 (d, 3H), 1.27 (d, 3H), 2.54 (m, 2H), 2.84 (m, 1H), 2.97 (m, 1H), 3.58 (br, 2H), 4.38 (t, 1H), 7.08 (d, 1H), 7.22 (t, 1H), 7.32 (m,4H), 7.65 (dd, 1H), 7.83 (d, 1H), 9.80 (s, 1H), 9.86 (br, 1H) 10.99 (s, 1H). Anal. ($C_{22}H_{29}NO_2.HCl$) H, N; C: calcd, 70.3; found, 70.8.

The starting compound (R)-N,N-diisopropyl-3-(5-formyl-2-hydroxy-phenyl)-3-phenylpropanamine was prepared as follows:

7.1 (R)-N,N-Diisopropyl-3-(5-formyl-2-hydroxyphenyl)-3-phenylpropanamine

DDQ (1.1 eq) was added to a solution of (R)-N,N-diisopropyl-3-(2-hydroxy-5-hydroxymethylphenyl)-3-phenylpropanamine mandelate (prepared as described in WO 94/11337, Example 1) (2.46 g, 5 mmol), dichloromethane (20 mL) and phosphate buffer (pH 7) (0.1 mL). Thereafter, sodium hydroxide solution (20 mL, 1 M) and diethyl ether were added and the phases were separated. The water-phase was extracted twice with dichloromethane-diethyl ether (2:1). The organic phase was dried (MgSO$_4$) and evaporated. The residue was crystallised from ethyl acetate-hexane to yield 1.35 g (80%).

EXAMPLE 8

(R)-N,N-Diisopropyl-3-[5-(7-hydroxy-2-aza-5-oxaheptyl)-2-hydroxyphenyl]-3-phenylpropanazine di-(S)-mandelate Sodiumcyanoborohydride (0.25 g, 3.9 mmol) was added to a solution of (R)-N,N-diisopropyl-3-(5-formyl-2-hydroxyphenyl)-3-phenylpropanamine (Example 7.1), (1.25 g, 3.7 mmol) and 2-ethoxy-(2-amino)-ethanol (19.5 g, 18 mmol) in methanol (10 mL). Hydrochloric acid (conc) was added to adjust pH to about 3. After 3 h, the pH was adjusted to about 1 and the solvent was evaporated. The residue was partioned between diethyl ether and water, whereafter the organic layer was evaporated and the residue chromatographed on silica (chloroform-triethylamine-methanol 88:10:2). The pure amine was dissolved in 2-propanol-diethyl ether with (S)-mandelic acid (2 eq), whereby the product crystallised (the crystals were unstable and an oily mass was soon obtained). Yield 0.2 g (7%); mp dec. $^1$H NMR (free amine) (CDCl$_3$-d) δ1.05 (d, 6H), 1.09 (d, 6H), 2.10 (m, 1H), 2.35 (m, 2H), 2.67 (m, 3H), 3.19 (m, 2H), 3.47 (m, 2H), 3.49 (t, 2H), 3.56 (d, 2H), 3.63 (t, 2H), 4.45 (dd, 1H), 6.75 (d, 1H), 6.79 (d, 1H), 6.95 (dd, 1H), 7.18 (m, 1H) and 7.26–7.33 (m, 4H).

EXAMPLE 9

(R)-N,N-Diisopropyl-3-(2-hydroxy-5-methyloxycarbonyl-phenyl)-3-phenylpropanamine hydrochloride A solution of (R)-N,N-diisopropyl-3-(2-benzyloxy-5-methyloxycarbonyl-phenyl)-3-phenylpropanamine (prepared as described in WO 94/11337, Example 1) (0.92 g, 2 mmol) in ethanol (30 mL) was hydrogenated over Pd/C (10%, 50 mg) at room temperature for 2 h. The catalyst was filtered off and the solution was treated with hydrogen chloride to obtain the amine salt. Yield 0.66 g (81%); mp 177–178° C.; [α]$_D$=−23° (c 1.0, methanol). $^1$H NMR (DMSO-d6) δ1.19 (dd, 6H), 1.25 (dd, 6H), 2.48 (m, 2H), 2.85 (m, 1H), 2.95 (m, 1H), 3.58 (m, 2H), 3.78 (s, 3H), 4.38 (t, 1H), 6.98 (d, 1H), 7.20 (m, 1H), 7.31 (d, 2H), 7,32 (s, 2H), 7.69 (dd, 1H), 7.81 (d, 1H), 9.85 (br, 1H), 10.74 (s, 1H). Anal. ($C_{23}H_{31}NO_3.HCl$) H, N, C.

EXAMPLE 10

N,N-Diisopropyl-3-(2-hydroxymethyl)phenyl-3-phenylpropanamine hydrochloride

A solution of N,N-diisopropyl-3-(2-carboxyphenyl)-3-phenylpropanamine hydrochloride (1.88 g, 5 mmol) in THF (30 mL) was added to LAH (1.5 g, 38 mmol) and the reaction mixture was stirred att ambient temperature for 2 h. The reaction was quenched and the solvent evaporated. The residue was dissolved in hot diethyl ether-2-propanol (100 mL, 1:4), whereafter HCl in diethyl ether was added. After cooling the product was filtered and dried at 60° C. (vacuum). Yield 1.2 g (68%); mp 223–224° C. $^1$H NMR (DMSO-d6) δ1.18 (t, 6H), 1.25 (q, 6H), 2.91 (m, 2H), 3.26 (disturbed by solvent, 2H), 3.57 (m, 2H), 4.38 (t, 1H), 4.43 (d, 1H), 4.74 (d, 1H), 5.22 (s, 1H), 7.20 (q, 2H), 7.25–7.35 (m, 5H), 7.40 (dd, 2H), 9.95 (s, 1H). Anal. ($C_{22}H_{31}NO.HCl$) H, N, C.

EXAMPLE 11

(S)-N,N-Diisopropyl-3-[2-hydroxy-5-(2-hydroxyethyl)phenyl]-3-phenylpropanamine hydrochloride (S)-N,N-Diisopropyl-3-[2-benzyloxy-5-(2-hydroxyethyl) phenyl]-3-phenylpropanamine (0.67 g, 1.5 mmol) was hydrogenated over Pd/C (10%, 67 mg) at atmospheric pressure overnight in ethanol (20 mL). The catalyst was filtered off and the solvent was evaporated. The residue was partioned between diethyl ether and sodium hydroxide (1 M). The aqueous layer was extracted with diethyl ether. The combined organic layers were washed with water, dried ($MgSO_4$) and the solvent was evaporated. The amine salt was obtained by dissolving the amine in diethyl ether-isopropanol and treatment with hydrogen chloride in diethyleter. Yield 0.37 g; mp 219–221° C.; [α]$_D$ –11.4° (c=1.0, methanol); $^1$H NMR (CD$_3$OD) δ1.30 (d, 12H), 2.36–2.60 (m, 2H), 2.68 (t, 2H), 3.05 (t, 2H), 3.60–3.72 (m, 4H), 4.40 (t, 1H), 6.73 (d, 1H), 6.90 (dd, 1H), 7.0 (s, 1H), 7.17–7.38 (m, 5H). Anal. ($C_{23}H_{33}NO_2.HCl.0.2H_2O$) C, H, N.

The starting compound (S)-N,N-diisopropyl-3-[2-benzyloxy-5-(2-hydroxy)ethylphenyl]-3-phenylpropanamine was prepared as follows:

11.1 (S)-N,N-Diisopropyl-3-(2-benzyloxy-5-ethenylphenyl)-3-phenylpropanamine A mixture of (S)-N,N-diisopropyl-3-(2-benzyloxy-5-bromophenyl)-3-phenylpropanamine (prepared as described in WO 94/11337, Example 1) (8 g, 12.7 mmol), Pd(OAc)$_2$ (28 mg, 0.12 mmol), tri-o-tolyl-phosphine (74 mg, 0.14 mmol) and tributylamine (5.9 mL, 24.5 mmol) in dimethylacetamide (50 mL) was heated to 60° C. under nitrogen atmosphere. Ethene (g) was then added to 8 bars pressure. After stirring overnight the reaction mixture was allowed to cool to room temperature. Nitrogen was flushed through the reaction vessel, and toluene and water were added. The aqueous layer was extracted with toluene and the combined organic layers were dried (MgSO$_4$) and concentrated. The residue was treated with sodium hydroxide (1 M) and extracted with diethyl ether and toluene. The organic layer was dried (MgSO$_4$) and concentrated in vacuo. The residue was chromatographed on silica (gradient ethyl acetate-methanol 90:10 up to 0.06% NH$_3$ in ethyl acetate-methanol 90:10) Yield 1 g (18%); $^1$H NMR (CDCl$_3$) δ0.94 (d, 12H), 2.20 (br, 2H), 2.37 (br, 2H), 3.0 (br, 2H), 4.38 (t, 1H), 5.0 (s, 2H), 5.11 (d, 1H), 5.61 (d, 1H), 6.60–6.70 (m, 1H), 6.80 (d, 1H), 7.12–7.19 (m, 12H).

11.2 (S)-N,N-Diisopropyl-3-[2-benzyloxy-5-(2-hydroxyethyl)phenyl]-3-phenylpropanamine (S)-N,N-Diisopropyl-3-(2-benzyloxy-5-ethenylphenyl)-3-phenylpropanamine (1 g, 2.34 mmol) in THF (25 mL) was added to 9-BBN (0.5 M in THF, 11.7 mL, 5.85 mmol) under nitrogen atmosphere at 0° C. Additional 9-BBN (2.3 mL, 1.2 mmol) was added after 3 hours of stirring, the temperature was raised to room temperature and the mixture was stirred for 0.5 hour. It was then cooled to 0° C. and 1 M sodium hydroxide (10 mL) was added followed by H$_2$O$_2$ (30% in H$_2$O, 10 mL). After 1 hours stirring, water was added and the mixture was extracted with diethyl ether. The organic layer was washed with water and brine, dried (MgSO$_4$) and concentrated. The residue was chromatographed on silica (gradient of diethyl ether to 1% NH$_3$ in diethyl ether). Yield 0.67 g (64%). $^1$H NMR (CDCl$_3$) δ0.90 (d, 12H), 2.10–2.18 (m, 2H), 2.30–2.37 (m, 2H), 2.80 (t, 2H), 2.90–3.0 (m, 2H), 3.80 (br, 2H), 4.40 (t, 1H), 5.0 (s, 2H), 6.80 (d, 1H), 7.0 (m, 1H), 7.10–7.38 (m, 11H).

EXAMPLE 12

(R)-N,N-Diisopropyl-3-[2-hydroxy-5-(2-hydroxyethyl)phenyl]-3-phenylpropanamine hydrochloride The title compound as well as the starting compounds were prepared in an analogous manner to the preparation described in Example 11, with the exception that (S)-N,N-diisoproyly-3-(2-benzyloxy-5-bromophenyl)-3-phenylpropanamine was changed to (R)-N,N-diisopropyl-3-(2-benzyloxy-5-bromophenyl)-3-phenylpropanamine (prepared as described in WO 94/11337, Example 1).

Yield 0.35 g (33%); mp 209–215° C.; [α]$_D$+9.80° (c=1.0, methanol); $^1$H NMR (CD$_3$OD) δ1.29 (d, 12H), 2.40–2.60 (m, 2H), 2.67 (t, 2H), 3.04 (t, 2H), 3.61–3.72 (m, 4H), 4.40 (t, 1H), 6.70 (d, 1H), 6.90 (dd, 1H), 7.0 (s, 1H), 7.18–7.40 (m, 5H). Anal. ($C_{23}H_{33}NO_2.HCl.0.2H_2O$) C, H, N.

Preparation of starting compounds:

12.1 (R)-N,N-Diisopropyl-3-(2-benzyloxy-5-ethenylphenyl)-3-phenylpropanamine Yield 5.5 g (53%); $^1$H NMR (CDCl$_3$) δ0.94 (d, 12H), 2.20 (br, 2H), 2.37 (br, 2H), 3.0 (br, 2H), 4.38 (t, 1H), 5.0 (s, 2H), 5.11 (d, 1H), 5.61 (d, 1H), 6.60–6.70 (m, 1H), 6.80 (d, 1H), 7.12–7.19 (m, 12H).

12.2 (R)-N,N-Diisopropyl-3-[2-benzyloxy-5-(2-hydroxyethyl)phenyl]-3-phenylpropanamine Yield 1.2 g (75%); $^1$H NMR (CDCl$_3$) δ0.89 (d, 12H), 2.15 (m, 2H), 2.32 (m, 2H), 2.80 (t, 2H), 2.95 (m, 2H), 3.80 (br, 2H), 4.40 (t, 1H), 4.98 (s, 2H), 6.80 (d, 1H), 6.96 (m, 1H), 7.10–7.35 (m, 11H).

EXAMPLE 13

(R)-N,N-Diisopropyl-3-(5-acetyl-2-hydroxyphenyl)-3-phenylpropanamine hydrochloride (R)-N,N-Diisopropyl-3-(5-acetyl-2-benzyloxyphenyl)-3-phenylpropanamine (1 g, 2.25 mmol) was treated as described in Example 11. Yield 0.6 g (68%); mp 105–115° C.; [α]$_D$ –32.6° (c 1.02, methanol); $^1$H NMR (DMSO-d$_6$) d 1.18–1.28 (m, 12H), 2.5 (m, 3H), 2.50–2.62 (m, 2H), 2.86 (m, 1H), 2.97 (m, 1H), 3.58 (m, 2H), 4.38 (t, 1H), 6.99 (d, 1H), 7.2 (m, 1H), 7.29–7.35 (m, 4H), 7.73 (dd, 1H), 7.85 (d, 1H), 9.90 (br, 1H), 10.70 (s, 1H). Anal. ($C_{23}H_{31}NO_2.HCl.0.4H_2O$) C, H, N.

The starting compound (R)-N,N-diisopropyl-3-(5-acetyl-2-benzyloxyphenyl)-3-phenylpropanamine was prepared as follows:

13.1 (R)-N,N-Diisopropyl-3-(5-acetyl-2-benzyloxyphenyl)-3-phenylpropanamine

To a stirred solution of (R)-N,N-diisopropyl-3-(2-benzyloxy-5-bromophenyl)-3-phenylpropanamine (Example 12) (10.2 g, 21.23 mmol) in DMF (100 mL) under nitrogen atmosphere at room temperature were sequentially added triethylamine (2.58 g, 25.47 mmol), TlOAc (6.15 g, 23.35 mmol), isobutylvinylether (14 mL, 106.14 mmol), DPPP (0.87 g, 2.12 mmol) and Pd(OAc)$_2$ (0.24 g, 1.06 mmol). The reaction temperature was raised to 100° C. and stirred for 3 hours, cooled to room temperature, filtered and treated with HCl (5%, 250 mL) and stirred for another 2 hours. The reaction mixture was repeatedly extracted with dichloromethane and the combined organic layers were dried (MgSO$_4$), filtered and the solvent evaporated. Triethylamine and DMF were destined off under reduced pressure to yield 9 g (98%); $^1$H NMR (CDCl$_3$) δ1.22 (m, 12H), 2.52–2.70 (m, 7H), 3.40 (br, 2H), 4.34 (t, 1H), 5.10 (s, 1H), 6.90 (d, 1H), 7.17–7.40 (m, 10H), 7.82 (m, 1H) and 7.92 (s, 1H).

EXAMPLE 14

N,N-Diisopropyl-3(R)-[2-hydroxy-5-(1-hydroxyethyl)phenyl]-3-phenylpropanamine fumarate N,N-Diisopropyl-3(R)-[2-benzyloxy-5-(1-hydroxyethyl)phenyl]-3-phenylpropanamine (2.7 g, 6.05 mmol) was hydrogenated over Pd/C (0.27 g, 10%) in ethanol at atmospheric pressure for 2 hours. The catalyst was filtered off and the solvent was evaporated. The resulting oil was chromatographed on silica (toluene-triethylamine 90:10). Fumarate salt of the amine was afforded by adding fumaric acid (0.13 g, 1.13 mmol) dissolved in warm ethanol to a solution of the free base in diethyl ether yielding white crystals (0.44 g, 83%); mp 240–244° C.; [α]$_D$ +9.80 (c 1.02, methanol); $^1$H NMR (DMSO-d$_6$) δ1.05 (d, 6H), 1.26 (dd, 3H), 2.20–2.30 (m, 2H), 2.55–2.67 (m, 2H), 3.30 (m, 2H), 4.32 (t, 1H), 4.59 (q, 1H), 6.53 (s, 2H), 6.72 (dd, 1H), 6.93 (dd, 0.5H), 7.12–7.17 (m, 1H), 7.21–7.31 (m, 5H). Anal. (C$_{23}$H$_{33}$NO$_2$.C$_4$H$_4$O$_4$.0.3H$_2$O) C, H, N.

The starting compound N,N-diisopropyl-3(R)-[2-benzyloxy-5-(1-hydroxyethyl)phenyl]-3-phenylpropanamine was prepared as follows:

14.1 N,N-Diisopropyl-3(R)-[2-benzyloxy-5-(1-hydroxyethyl)phenyl]-3-phenylpropanamine N,N-Diisopropyl-3(R)-(5-acetyl-2-benzyloxyphenyl)-3-phenylpropanamine, prepared as described in Example 13.1, (3.5 g, 7.90 mmol) dissolved in dry THF was added to LiAlH$_4$ (0.2 g, 5.41 mmol). After 2 hours of stirring, additional LiAlH$_4$ (50 mg, 1.32 mmol) was added and the reaction mixture was stirred for 1.5 hours. The reaction was quenched and the solvent evaporated. The residue was chromatographed on silica (toluene-E$_3$N 90:10) to give 2.74 g (78%) of an oil that crystallised slowly upon storage at room temperature.

EXAMPLE 15

(+)-N,N-Diisopropyl-3(R)-[5-(1(R*),2-dihydroxyethyl)-2-hydroxyphenyl]-3-phenylpropanamine fumarate N,N-Diisopropyl-3(R)-[2-benzyloxy 5-(1(R*),2-dihydroxyethyl)phenyl]-3-phenylpropanamine (0.55 g, 1.2 mmol) was treated in an analogous manner to that described in Example 14 above, which yielded white crystals, 0.32 g (55%); mp 196–200° C.; [α]$_D$ +13.50 (c 1.0, methanol); $^1$H NMR (CD$_3$OD) δ1.28 (m, 12H), 2.40–2.48 (m, 1H), 2.52–2.60 (m, 1H), 3.03 (t, 2H), 3.55 (d, 2H), 3.66 (m, 2H), 4.42 (t, 1H), 4.57 (t, 1H), 6.7 (s, 2H), 6.79 (d, 1H), 7.05 (dd, 1H), 7.16–7.21 (m, 2H), 7.28 (m, 2H), 7.36 (m, 2H). Anal. (C$_{23}$H$_{33}$NO$_3$.C$_4$H$_4$O$_4$) C, H, N.

The starting compound N,N-diisopropyl-3(R)-[2-benzyloxy-5-(1(R*),2-dihydroxyethyl)phenyl]-3-phenylpropanamine was prepared as follows:

15.1 N,N-Diisopropyl-3(R)-[2-benzyloxy-5-(1(R*),2-dihydroxyethyl)phenyl]-3-phenylpropanamine To an ice-chilled solution of AD-mix-α (5.7 g) in H$_2$O (20 mL) and t-BuOH (10 mL) was added N,N-diisopropyl-3(R)-(2-benzyloxy-5-ethenylphenyl)-3-phenylpropanamine (Example 12.1), (1.74 g, 4.1 mmol) dissolved in t-BuOH (10 mL). After 1 hour of stirring, the ice bath was removed and the reaction mixture was stirred for additional 21 hours. Na$_2$SO$_3$ (6 g) was then added and after 1 hours of stirring the reaction mixture was partioned between H$_2$O and ethyl acetate. The aqueous layer was extracted 3 times with ethyl acetate, the combined organic layers were dried (MgSO$_4$) and the solvent evaporated. The residue was chromatographed on silica (ethyl acetate-triethylamine, 90:10) to afford 0.55 g. $^1$H NMR (CDCl$_3$) δ0.9 (s, 6H), 0.95 (s, 6H), 2.15–2.20 (m, 2H), 2.30–2.38 (m, 2H), 2.96 (m, 2H), 3.60–3.70 (m, 2H), 4.41 (t, 1H), 4.75 (m, 1H), 5.0 (s, 2H), 6.85 (d, 1H), 7.10–7.35 (m, 12H).

EXAMPLE 16

(−)-N,N-Diisopropyl-3(R)-[5-(1(S*),2-dihydroxyethyl) 2-hydroxyphenyl]-3-phenylpropanamine fumarate N,N-Diisopropyl-3(R)-[2-benzyloxy-5-(1(S*),2-dihydroxyethyl)phenyl]-3-phenylpropanamine (1.1 g, 2.4 mmol) was treated in an analogous manner to that described in Example 11 which yielded white crystals, 0.25 g (21%); mp 208–211° C.; [α]$_D$ −8° (c 1.02, methanol); $^1$H NMR (CD$_3$OD) δ1.28 (m, 12H), 2.39–2.47 (m, 1H), 2.51–2.59 (m, 1H), 3.03 (t, 2H), 3.51–3.53 (m, 2H), 3.67 (m, 2H), 4.42 (t, 1H), 4.54 (dd, 1H), 6.68 (s, 2H), 6.78 (d, 1H), 7.06 (dd, 1H), 7.16–7.20 (m, 2H), 7.26 (m, 2H), 7.34–7.36 (m, 2H). Anal. (C$_{23}$H$_{33}$NO$_3$.C$_4$H$_4$O$_4$) C, H, N.

The starting compound N,N-diisopropyl-3(R)-[2-benzyloxy-5-(1(S*),2-dihydroxyethyl)phenyl]-3-phenylpropanamine was obtained by treating N,N-diisopropyl-3(R)-(2-benzyloxy-5-ethenylphenyl)-3-phenylpropanamine (obtained in Example 12.1) as described in Example 15.1 above, but with AD-mix-β replacing AD-mix-α. Yield 1.2 g (44%).

EXAMPLE 17

(R)-[N,N-Diisopropyl-3-[2-hydroxy-5-(6-hydroxyhexyl)phenyl]-3-phenylpropanamine hydrochloride N,N-Diisopropyl-3(R)-[2-benzyloxy-5-(6-hydroxyhexyl-1-enyl)phenyl]-3-phenylpropanamine (0.35 g, 0.72 mmol) was treated in an analogous manner to that described in Example 14. Yield 0.10 g (31%); mp 147–156° C.; [α]$_D$ +8.2° (c 1.01, methanol); $^1$H NMR (CD$_3$OD) δ1.25–1.32 (m, 16H), 1.45–1.54 (m, 4H), 2.40–2.48 (m, 3H), 2.51–2.59 (m, 1H), 3.0–3.10 (m, 2H), 3.51 (t, 2H), 3.68 (m, 2H), 4.40

(t, 1H), 6.72 (d, 1H), 6.86 (dd, 1H), 6.91 (d, 1H), 7.19 (m, 1H), 7.30 (t, 2H), 7.34–7.36 (m, 2H). Anal. ($C_{27}H_{41}NO_2 \cdot HCl \cdot 2H_2O$) C, N; H: calcd, 9.6; found, 8.3.

The starting compound (R)-N,N-diisopropyl-3-[2-benzyloxy-5-(6-hydroxyhexyl-1-enyl)phenyl]-3-phenylpropanamine was prepared as follows:

17.1 (R)-N,N-Diisopropyl-3-(2-benzyloxy-5-formylphenyl)-3-phenylpropanamine.

n-BuLi (2.5 M in hexane, 19 mL, 47.5 nmol) was added to a solution of to (R)-N,N-diisopropyl-3-(2-benzyloxy-5-bromophenyl)-3-phenylpropanamine (prepared as described in WO 94/11337, Example 1) (8.9 g, 18.52 mmol) in dry diethyl ether (100 mL) kept at −40° C. under nitrogen atmosphere. After 1.5 hour of stirring, additional n-BuLi (10 mL, 25 mmol) was added and after 2 hours another n-BuLi (5 mL, 12.5 mmol) was added. The reaction was then stirred for 15 minutes and DMF (6 mL, 77.8 mmol) was added followed by additional DMF (5 mL, 64.8 mmol) after 20 minutes of stirring. The temperature was allowed to rise to room temperature and after 35 minutes of stirring, $NH_4Cl$ (sat.) was added followed by water and diethyl ether. The layers were separated and the aqueous layer was extracted with diethyl ether. The combined organic layers were dried ($MgSO_4$) and the solvent was evaporated. The residue was chromatographed on silica (toluene-triethylamine 90:10) to afford 8 g (100%) of a yellowish oil; $^1H$ NMR ($CDCl_3$) δ0.90 (m, 12H), 2.12–2.40 (m, 4H), 2.95 (m, 2H), 4.44 (t, 1H), 5.10 (s, 2H), 6.95 (d, 1H), 7.15–7.36 (m, 10H), 7.70 (dd, 1H), 7.91 (s, 1H), 9.88 (s, 1H).

17.2 (R)-N,N-Diisopropyl-3-[2-benzyloxy 5-(5-carboxypent-1-enyl)phenyl]-3-phenylpropanamine To a slurry of 4-carboxybutyl triphenylphosphonium bromide (4.1 g, 9.31 mmol) in THF (25 mL) at −10° C. under nitrogen atmosphere was added potassium tert-butoxide (2.1 g, 18.62 mmol). The mixture turned orange and after 10 minutes stirring, (R)-N,N-diisopropyl-3-(2-benzyloxy-5-formylphenyl)-3-phenylpropanamine (2 g, 4.65 mmol) in THF (10 mL) was added. After 4 hours of stirring, hydrochloric acid (1M) and diethyl ether were added and the layers were separated. The aqueous layer was extracted with ethyl acetate. The combined organic layers were dried ($MgSO_4$) and the solvent was evaporated. The residue was chromatographed on silica (ethyl acetate-triethylamine 90:10 followed by methanol) to afford 3 g containing traces of triphenylphosphine. The product was used in the next step without further purification.

17.3 (R)-N,N-Diisopropyl-3-[2-benzyloxy-5-(6-hydroxyhex-1-enyl)phenyl]-3-phenylpropanamine (R)-N,N-Diisopropyl-3-[2-benzyloxy-5-(5-carboxypent-1-enyl)phenyl]-3-phenylpropanamine was reduced as described in Example 10. Yield 0.35 g (15%).

EXAMPLE 18

(R)-N,N-Diisopropyl-3-[5-(2-diisopropylaminoethyl)-2-hydroxyphenyl]-3-phenylpropanamine hydrochloride (R)-N,N-Diisopropyl-3-[2-benzyloxy-5-(2-diisopropylaminoethyl)phenyl]-3-phenylpropanamine (0.6 g, 1.13 mmol) was refluxed with concentrated HCl (25 mL) overnight. The reaction mixture was then basified with 10 M sodium hydroxide and extracted with diethyl ether. The organic layer was dried ($MgSO_4$) and concentrated in vacuo to give 0.5 g oil that was fractionated on a reversed-phase PEP-RPC HR 30/26 column using a gradient of acetonitrile (containing 0.1% TFA) and milliQ-water (containing 0.1% TFA). The pure fractions were pooled and extracted with diethyl ether and 10 M sodium hydroxide. The resulting diethyl ether solution was treated with hydrogen chloride in diethyl ether. Yield 50 mg (9%); $[\alpha]_D$ +1.4° (c 0.94, methanol); $^1H$ NMR ($CD_3OD$) δ1.27–1.34 (m, 12H), 1.36–1.42 (m, 12H), 2.50–2.58 (m, 1H), 2.60–2.67 (m, 1H), 2.95 (t, 2H), 3.05 (m, 2H), 3.15–3.27 (m, 2H), 3.70 (m, 2H), 3.75 (m, 2H), 4.40 (t, 1H), 6.80 (d, 1H), 7.02 (dd, 1H), 7.13 (d, 1H), 7.20 (m, 1H), 7.31 (m, 1H), 7.39–7.41 (m, 1H). Anal. ($C_{29}H_{46}N_2O \cdot 2HCl \cdot 0.4H_2O$) C, H, N.

The starting compound N,N-diisopropyl-3(R)-[2-benzyloxy-5-(2-diisopropylaminoethyl)phenyl]-3-phenylpropanamine was prepared as follows:

18.1 N,N-Diisopropyl-3(R)-(5-formylmethyl-2-benzyloxyphenyl)-3-phenylpropnamine DMSO (1.1 mL, 15.5 mmol) dissolved in dichloromethane was added dropwise to oxalyl chloride (0.64 mL, 7.74 mmol) at −78° C. under nitrogen atmosphere. After 10 minutes of stirring, (R)-N,N-diisopropyl-3-[2-benzyloxy-5-(2-hydroxyethyl)phenyl]-3-phenylpropanamine (Example 12.2) (2.3 g, 5.16 mmol) in dichloromethane was added and the reaction mixture was stirred for additional 1 h. Triethylamine (5.4 mL, 38.7 mmol) was then added and the temperature was allowed to rise to room temperature. The reaction mixture was taken up in water and dichloromethane. The organic layer was dried ($MgSO_4$) and concentrated in vacuo and the product was used in the next step without further purification.

18.2 (R)-N,N-Diisopropyl-3-[2-benzyloxy-5-(2-diisopropylaminoethyl)phenyl]-3-3-phenylpropanamine Diisopropylamine (4.2 mL, 30 mmol) was dissolved in methanol (12 mL). 5 M HCl in methanol (2 mL) was added followed by N,N-diisopropyl-3(R)-(5-formylmethyl-2-benzyloxyphenyl)-3-phenylpropanamine (5 mmol) in methanol (10 mL) and sodium cyanoborohydride (0.22 g, 3.5 mmol). The reaction mixture was stirred at room temperature overnight. methanol was then evaporated, and diethyl ether and $H_2O$ were added. The organic layer was dried ($MgSO_4$) and concentrated in vacuo to give 3 g of a crude product that was chromatographed on silica (toluene-triethylamine 95:5). Yield 0.65 g (25%); $^1H$ NMR ($CDCl_3$) δ0.88–0.91 (m, 18H), 1.20 (d, 9H), 2.10–2.20 (m, 2H), 2.30–2.38 (m, 2H), 2.87–3.10 (m, 4H), 4.34 (m, 1H), 4.98 (d, 2H), 6.75–6.97 (m, 2H), 7.10–7.30 (m, 11H).

EXAMPLE 19

(R)-N,N-Diisopropyl-3-(5-ethoxymethyl-2-hydroxyphenyl)-3-phenylpropanamine (R)-N,N-Diisopropyl-3-(2-hydroxy-5-hydroxymethylphenyl)-3-phenylpropanamine (prepared as described in WO 94/11337, Example 1) (3.9 g, 11.5 mmol) and $Al_2O_3$ (115 g, 1.13 mol) refluxed in ethyl acetate (0.5 L) for 60 hours. $Al_2O_3$ was filtered off and ethyl acetate was evaporated. Chromatography on silica (toluene-triethylamine, 90:10) of the residue yielded 2.5 g (59%). The fumarate salt was obtained by adding fumaric acid (0.17 g, 1.48 mmol) dissolved in warm ethanol to the free base (0.55 g, 1.48 mmol) in diethyl ether; mp 174–177° C.; $[\alpha]_D$ +5.5°

(c 1.02, methanol); $^1$H NMR (CD$_3$OD) δ1.15 (t, 3H), 1.27–1.30 (m, 12H), 2.41–2.49 (m, 1H), 2.52–2.60 (m, 1H), 3.04 (dd, 2H), 3.49 (q, 2H), 3.67 (m, 2H), 4.35 (s, 2H), 4.43 (t, 1H), 6.69 (s, 2H), 6.80 (d, 1H), 7.04 (dd, 1H), 7.12 (d, 1H), 7.18–7.37 (m, 4H). Anal. (C$_{24}$H$_{35}$NO$_2$.C$_4$H$_4$O$_4$) C, H, N.

EXAMPLE 20

N-Isopropyl-3-(5-carboxy-2-hydroxyphenyl)-3-phenylpropanamine hydrochloride

N-Benzyl-N-isopropyl-3-(2-benzyloxy-5-carboxyphenyl)-3-phenylpropanamine (1.3 g, 2.6 mmol) was dissolved in HOAc. Palladium (10%) on charcoal (0.13 g) was added and the mixture was hydrogenated at atmospheric pressure for 48 hours. The catalyst was then filtered off and the solvent was evaporated. The resulting oil was fractionated on a reversed-phase PEP-RPC HR 30/26 column using a gradient of acetonitrile (containing 0.1% TFA) and milliQ-water (containing 0.1% TFA). This purification was done in 16 portions with about 100 mg material each time. The pure fractions were pooled and freeze-dried to give 0.57 g of trifluoroacetic acid salt. The crystals were dissolved in 1 M HCl and freeze-dried to give 0.4 g (43%) of the hydrochloride salt as white crystals; mp 155–160° C.; $^1$H NMR (DMSO-d$_6$) δ1.17 (d, 3H), 1.19 (d, 3H), 2.30–2.38 (m, 1H), 2.38–2.46 (m, 1H), 2.72 (br, 1H), 2.80 (br, 1H), 3.25 (m, 1H), 4.40 (t, 1H), 6.94 (d, 1H), 7.18–7.22 (m, 1H), 7.29–7.33 (m, 4H), 7.66 (dd, 1H), 7.76 (d, 1H); Anal. (C$_{19}$H$_{23}$NO$_3$.HCl.0.5H$_2$O) C, H, N.

The starting compound N-benzyl-N-isopropyl-3-(2-benzyloxy-5-carboxyphenyl)-3-phenylpropanamine was prepared as follows:

20.1 3-(2-Benzyloxy-5-bromophenyl)-3-phenylpropanal 3-(2-Benzyloxy-5-bromophenyl)-3-phenylpropanol (16 5 g, 41.5 mmol) (prepared as described in WO 94/11337, Example 1c) was reacted as described in Example 18.1. The combined organic layers were washed with 2 M HCl, 10% NaHCO$_3$, water and brine, dried (MgSO$_4$) and evaporated to give 16 g (98%) of yellowish crystals of the product that was used in the next step without further purification; mp 99–100° C.; $^1$H NMR (CDCl$_3$) δ3.10 (dd, 2H), 5.0 (s, 2H), 4.98–5.10 (m, 1H), 6.76 (d, 1H), 7.16–7.38 (m, 12H), 9.65 (s, 1H).

20.2 N-Benzyl-N-isopropyl-3-(2-benzyloxy-5-bromophenyl)-3-phenylpropanamine

To a solution of N-benzylisopropylamine (34 mL, 0.20 mol) in methanol (80 mL) was added 5 M HCl in methanol (16.2 mL, 80.9 mmol) followed by 3-(2-benzyloxy-5-bromophenyl)-3-phenylpropanal (16.0 g, 40.5 mmol) in methanol (20 mL) and sodium cyanoborohydride (1.78 g, 28.3 mmol). The resulting solution was stirred for 17 hours. The solvent was evaporated and diethyl ether was added to the resulting syrup. The solution was washed 3 times with water, dried over MgSO$_4$ and evaporated. The residue was chromatographed on silica (hexane-ethyl acetate, 75:25) giving 15.9 g of a syrup. The hydrochloride salt of the compound was prepared by dissolving the product in diethyl ether and adding HCl dissolved in diethyl ether. The resulting oil was washed with diethyl ether, dissolved in 10 M sodium hydroxide and extracted with diethyl ether 3 times. Purification by chromatography on silica (using a gradient of dichloromethane up to 1% triethylamine in dichloromethane) yielded 7 g (33%) of the product as a colourless oil. $^1$H NMR (CDCl$_3$) δ0.84 (d, 3H), 0.90 (d, 3H), 2.02–2.12 (m, 2H), 2.38 (t, 2H), 2.90 (m, 1H), 3.50 (d, 2H), 4.50 (t, 1H), 4.95 (s, 2H), 6.70 (s, 1H), 7.10–7.35 (m, 17H).

20.3 N-Benzyl-N-isopropyl-3-(2-benzyloxy-5-carboxphenyl)-3-phenylpropanamine

A mixture of magnesium turnings (1.18 g, 48.6 mmol) and iodine (one small crystal) was warmed gently. A solution of N-benzyl-N-isopropyl-3-(2-benzyloxy-5-bromophenyl)-3-phenylpropanamine (6.0 g, 11 mmol) and 1,2-dibromoethane (0.2 mL, 2.3 mmol) in dry THF (25 mL) was added dropwise under nitrogen atmosphere to the refluxing mixture. After 2 hours of refluxing, 1,2-dibromoethane (0.59 mL, 6.8 mmol) was added. The mixture was left overnight under nitrogen atmosphere. The mixture was then added together with 1,2-dibromoethane (0.93 mL, 10.8 mmol) to warmed magnesium turnings (1.18 g, 48.6 mmol) and iodine (one small crystal). After 30 minutes of refluxing, the mixture was cooled to room temperature and CO$_2$ (g) was bubbled through. After 3 hours, ammonium chloride (aq, 15%, 50 mL) was added followed by diethyl ether (100 mL). The layers were separated and the organic layer was dried (MgSO$_4$) and concentrated to give 5.8 g of an oil. The crude product was chromatographed on silica (using a gradient of acetone up to 5% ethanol in acetone) to give the pure product (1.3 g, 23%) as an oil. N-benzyl-N-isopropyl-3-(2-benzyloxyphenyl)-3-phenylpropanamine (3.1 g) was obtained as a biproduct from the reaction. $^1$H NMR (CDCl$_3$) δ0.98 (d, 3H), 1.10 (d, 3H), 2.30–2.40 (m, 2H), 2.46–2.65 (m, 2H), 3.40 (br, 1H), 3.85 (br, 2H), 4.30 (br, 1H), 4.98 (br, 2H), 6.80 (d, 1H), 7.10–7.40 (m, 15H), 7.95 (d, 1H), 7.95 (d, 1H), 8.20 (s, 1H).

EXAMPLE 21

N-Benzyl-N-isopropyl-3-(2-hydroxyphenyl)-3-phenylpropanamine hydrochloride

N-Benzyl-N-isopropyl-3-(2-benzyloxy-5-carboxyphenyl)-3-phenylpropanamine, prepared as described in Example 20.3, (3.1 g, 6.90 mmol) was refluxed in concentrated HCl (30 mL) for 20 h. The reaction mixture was allowed to cool to room temperature and the liquid was poured off. The remaining oil was washed with water and diethyl ether and then dissolved in 2-propanol. The solution was evaporated and treated with 10 M sodium hydroxide to give the free base. Chromatography on silica (hexane:ethyl acetate 75:25) afforded 0.5 g of the compound that was fractionated on a reversed-phase PEP-RPC HR 30/26 column using a gradient of acetonitrile (containing 0.1% TFA) and milliQ-water (containing 0.1% TFA). The pure fractions were pooled and extracted with diethyl ether and 10 M sodium hydroxide. To the resulting diethyl ether solution was added dropwise saturated diethyl ether-HCl (g). The resulting crystals of the hydrochloric salt were collected by filtration; mp 115–122° C.; $^1$H NMR (DMSO-d$_6$) δ1.28 (m, 6H), 2.27–2.38 (m, 1H), 2.48–2.55 (m, 1H), 2.72–2.97 (m, 2H), 3.55 (m, 1H), 4.23 (m, 2H), 4.35 (m, 1H), 6.68–6.74 (m, 1H), 6.82 (dt, 1H), 6.96–7.24 (m, 7H), 7.38–7.42 (m, 3H), 7.64–7.68 (m, 2H), 9.55 (d, 1H), 10.62 (br, 1H). Anal. (C$_{25}$H$_{29}$NO.HCl) C, H, N.

EXAMPLE 22

(R)-N,N-Diisopropyl-3-[5-(3-aminopropyl)-2-hydroxyphenyl]-3-phenylpropanamine dihydrochloride (R)-N,N-Diisopropyl-3-[2-benzyloxy-5-(2-cyanoethenyl) phenyl]-3-phenylpropanamine (3.20 g, 7.07 mmol) was dissolved in 100% acetic acid and 10% Pd/C (0.52 g) was added. The mixture was hydrogenated (60 psi) overnight at room temperature. The catalyst was filtered off and the solvent was evaporated. The residue was dissolved in water, basified with sodium hydroxide (11 M), extracted with ethyl acetate, the organic phase was dried ($MgSO_4$), and evaporated. The residue was chromatographed on silica (toluene-ethyl acetate-triethylamine-methanol, 20:5:1.5:1). The amine was redissolved in diethyl ether and a HCl-saturated diethyl ether solution was carefully added. The precipitate was filtered off wich gave 0.30 g ( 10%); $^1$H NMR ($CD_3OD$) δ1.29 (m, 12H), 1.88 (m, 2H), 2.51((m, 2H), 2.59 (t, 2H), 2.88 (t, 2H), 3.04 (t, 2H), 3.68 (m, 2H), 4.40 (t, 1H), 4.55 (bs, 1H), 6.76 (d, 1H), 6.93 (d, 1H), 7.03 (s, 1H), 7.19 (t, 1H), 7.30 (t, 2H), 7.37 (d, 2H); mp. 226–228° C.; $[\alpha]_D$ +11.5° (c=1.0, methanol). Anal. ($C_{24}H_{36}N_2O*2HCl$) C, H, N.

The starting compound (R)-N,N-diisopropyl-3-[2-benzyloxy-5-(2-cyanoethenyl)phenyl]-3-phenylpropanamine was prepared as follows:

22.1 (R)-N,N-Diisopropyl-3-[2-benzyloxy-5-(2-cyanoethenyl)phenyl]-3-phenylpropylamine To a solution of (R)-N,N-diisopropyl-3-(2-benzyloxy-5-bromophenyl)-3-phenylpropanamine (13.87 g, 28.87 mmol) (prepared as described in WO 94/11337, Example 1) in DMF (140 mL) was added triethylamin (5.00 mL, 36.10 mmol), $Pd(OAc)_2$ (0.32 g, 1.44 mmol), tri(o-tolyl)phosphine (1.76 g, 5.77 mmol) and acrylonitrile (2.39 mL, 36.10 mmol). The reaction mixture was stirred overnight at 115° C. in a sealed flask equipped with a reflux condenser under nitrogen atmosphere. The resulting mixture was concentrated, and the residue was dissolved in diethyl ether, washed with aqueous 2 M sodium hydroxide and water. The organic phase was dried ($MgSO_4$) where after petroleum ether was added to the organic phase and a precipitate was formed. Recrystallisation from ethanol yielded 5.50 g (42%). $^1$H NMR ($CDCl_3$) δ0.90 (s, 6H), 0.95 (s, 6H), 2.15 (q, 2H), 2.35 (q, 2H), 2.95 (m, 2H), 4.40 (t, 1H), 5.05 (s, 2H), 5.70 (d, 1H), 6.85 (d, 1H), 7.10–7.50 (m, 13H).

EXAMPLE 23

(R)-N,N-Diisopropyl-3-[5-3-(acetamidopropyl)-2-hydroxyphenyl]-3-phenylpropanamine hydrochloride To a solution of (R)-N,N-diisopropyl-3-[5-(3-aminopropyl)-2-hydroxyphenyl]-3-phenylpropanamine, (Example 22), (0.45 g, 1.23 mmol) in methanol (45 mL) was added acetic anhydride (0.23 mL, 2.47 mmol). The mixture was stirred for 3 h at room temperature and then evaporated to dryness. The residue was dissolved in $H_2O$, basified with aqueous 11 M sodium hydroxide and extracted with toluene. The organic layer was dried with $MgSO_4$, filtered and evaporated. The amine was dissolved in diethyl ether and a HCl-saturated diethyl ether solution was carefully added. The precipitate formed was filtered off to give 0.55 g (100%). $^1$H NMR ($CD_3OD$) δ1.27 (m, 12H), 1.75 (m, 2H), 2.08 (s, 3H), 2.52 (m, 4H), 3.04 (t, 2H), 3.20 (t, 2H), 3.68 (m, 2H), 4.40 (t, 2H), 6.72 (d, 1H), 6.90 (d, 1H), 6.99 (s, 1H), 7.19 (t, 1H), 7.30 (m, 4H); mp. 171–175° C.; $[a]_D$ +3.6° (c=0.5, methanol). ($C_{26}H_{38}N_2O_2*HCl$) C, H, N.

EXAMPLE 24

(R)-N,N-Diisopropyl-3-[5-(2-cyanoethyl)-2-hydroxyphenyl]-3-phenylpropanamine hydrochloride (R)-N,N-Diisopropyl-3-[2-benzyloxy-5-(2-cyanoethenyl) phenyl]-3-phenylpropylamine (Example 22.1), (4.00 g, 8.84 mmol) was treated as described in Example 22, but the hydrogenation was performed at atmospheric pressure. Yield 1.35 g (38%); $^1$H NMR ($CD_3OD$) δ1.14 (s, 6H), 1.16 (s, 6H), 2.50 (m, 2H), 2.79 (t, 2H), 3.05. (t, 2H), 3.68 (m, 2H), 4.39 (t, 2H), 6,75 (d, 1H), 6.98 (d, 1H), 7.09 (s, 1H), 7.19 (t, 1H), 7.32 (m, 4H); mp. 156–159° C.; $[\alpha]_D$ +4.0° (c=0.5, methanol); Anal. ($C_{24}H_{32}N_2O*1.0HCl*0.25H_2O$) C, H; N: calcd, 6.9; found, 6.4.

EXAMPLE 25

(R)-N,N-Diisopropyl-3-[5-(2-carbamoylethyl)-2-hydroxyphenyl]-3-phenylpropanamine hydrochloride.

A solution of (R)-N,N-diisopropyl-3-[5-(2-cyanoethyl)-2-hydroxyphenyl]-3-phenylpropanamine (Example 24), (2.00 g, 5.48 mmol), in conc. HCl was stirred at 50° C. for 2 h and then evaporated. The residue was dissolved in water, basified with aqueous 11 M sodium hydroxide and extracted with toluene. The organic layer was dried ($MgSO_4$), filtrated and evaporated. The residue was chromatographed on toluene-ethyl acetate-triethylamine-methanol, 7:2:1:1. The product was obtained from dietyl ether-hydrogen choride. Yield 0.9 g (39%); $^1$H NMR ($CD_3OD$) δ1.31 (m, 12H), 2.44 (t, 2H), 2.53 (m, 2H), 2.78 (t, 2H), 3.04 (t, 2H), 3.67 (m, 2H), 4.39 (t, 1H), 6.72 (d, 1H), 6.82 (d, 1H), 7.02 (s, 1H), 7.18 (t, 1H), 7.32 (m, 4H); mp. 200–202° C.; $[\alpha]_D$ +7.6° (c=0.5, methanol). Anal. ($C_{24}H_{34}N_2O_2*1.0HCl*0.5H_2O$) C, H, N.

EXAMPLE 26

(R)-N,N-Diisopropyl-3-[5-(2-carboxyethyl)-2-hydroxyphenyl]-3-phenylpropanamine hydrochloride To a solution of (R)-N,N-diisopropyl-3-[5-(2-carbamoylethyl)-2-hydroxyphenyl]-3-phenylpropanamine (obtained in Example 25), (0.50 g, 1.31 mmol) in ethanol (15 mL) and $H_2O$ (10 mL) was added KOH (3.75 g, 66.8 mmol). The mixture was stirred overnight at 100° C. The solvent was evaporated and the residue redissolved in $H_2O$ and washed with diethyl ether. The aqueous layer was acidified with conc. HCl and the precipitate was collected by filtration and washed with 2 M HCl. The product was fractionated on a reversed-phase PEP RPC HR 30/26 (Pharmacia Biotech AB, Sweden) column using a gradient of 20–60% acetonitrile with 0.1% TFA. Fractions were pooled and hydrochloric acid (2 mL, conc.) was added and the solvent was evaporated. The residue was crystallised from methanol-diethyl ether to give 0.37 g (0.96 mmol, 74%); $^1$H NMR ($CD_3OD$) δ1.28 (m, 12H), 2.48 (m, 4H), 2.76 (t, 2H), 3.04 (t, 2H), 3.67 (m, 2H), 4.39 (t, 1H), 6.72 (d, 1H), 6.92 (d, 1H), 7.00 (s, 1H), 7.19 (t, 1H), 7.32 (m, 4H); mp. 205–207° C.; $[\alpha]_D$ +3.7° (c=1.0, methanol). Anal. ($C_{24}H_{33}NO_3*1.0HCl$) C, H, N.

EXAMPLE 27

(R)-(N,N-Diisopropyl-3-(5-amino-2-hydroxyphenyl)-3-phenylpropanamine dihydrochloride (R)-N,N-Diisopropyl-3-(5-azido-2-benzyloxyphenyl)-3-phenylpropanamine (0.90 g, 2.03 mmol) was dissolved in acetic acid and 10% Pd/C (210 mg, cat.) was added. The mixture was stirred and exposed to $H_2$ (1 atm.) at room temperature overnight. The Pd/C catalyst was filtered off, and the filtrate evaporated. The residue was dissolved in water and basified with aqueous 11 M sodium hydroxide, extracted with diethyl ether, dried (MgSO$_4$) filtrated and evaporated. The crude residue was chromatographed on silica (n-hexane-ethanol-triethylamine, 7:3:1). The hydrochloride was obtained from dietyl ether hydrogen chloride. The resulting oil was freeze-dried from water. Yield 0.30 g (37%); $^1$H NMR (DMSO) δ1.13–1.33 (m, 12H), 2.47 (m, 2H), 2.82 (br, 1H), 2.98 (br, 1H), 3.57 (br, 2H), 4.38 (t, 1H), 6.96 (d, 1H), 7.08 (d, 1H), 7.19 (s, 1H), 7.22 (m, 1H), 7.32 (m, 4H), 10.05 (br, 2H), 10.13 (s, 1H); mp. 180–183° C.; [α]$_D$ +21.0° (c=0.1, methanol). Anal. (C$_{21}$H$_{30}$N$_2$O*2.0HCl*0.5H$_2$O) C, H, N.

The starting compound (R)-N,N-diisopropyl-3-(5-azido-2-benzyloxyphenyl)-3-phenylpropanamine was prepared as follows:

27.1 (R)-N,N-Diisopropyl-3-(5-azido-2-benzyloxyphenyl)-3-phenylpropanamine

To a mixture of (R)-N,N-diisopropyl-3-(2-benzyloxy-5-bromophenyl)-3-phenylpropanamine (10.00 g, 20.81 mmol) (prepared as described in WO 94/11337, Example 1) and Mg (1.57 g, 64.52 mmol) in THF (50 mL) was added 1,2-dibromoethane (3.59 mL, 41.63 mmol) and the solution was self-refluxing for a while. The mixture was refluxed for 1 h whereafter the solution was cooled and tosyl azide (4.10 g, 20.81 mmol) in diethyl ether (100 mL) was added with constant stirring while keeping the temperature at 0° C. wherafter the temperature was allowed to rise to room temperature for 4 h. A solution of tetra-sodium pyrophosphate decahydrate (4.46 g, 10.00 mmol) in 50 mL water was added. A precipitate was filtered off and the filtrate was evaporated. The residue was extracted with diethyl ether, the organic phase was dried (MgSO$_4$) and evaporated. The residue was chromatographed on silica (n-hexane-ethanol, 8:2). The product was crystallised from ethanol to give 1.15 g (13%); IR (KBr) 2116 (N$_3$) cm$^{-1}$; $^1$H NMR (CDCl$_3$) δ0.92 (d, 12H), 2.10 (m, 2H), 2.33 (m, 2H), 2.95 (m, 2H), 4.40 (t, 1H), 5.00 (s, 2H), 6.81 (d, 2H), 6.97 (s, 1H), 7.10–7.40 (m, 10H).

EXAMPLE 28

(R)-N,N-Diisopropyl-3-(5-azido-2-hydroxyphenyl)-3-phenylpropanamine hydrochloride To a solution of (R)-N,N-diisopropyl-3-(5-amino-2-hydroxyphenyl)-3-phenylpropanamine (0.25 g, 0.76 mmol) in 0.78 M HCl (5.35 mL, 4.20 mmol) was added NaNO$_2$ (0.05 g, 0.76 mmol) dissolved in H$_2$O (0.4 mL) at –10° C. and the mixture was stirred for 20 minutes. To the mixture was added NaN$_3$, (57 mg, 0.88 mmol) dissolved in H$_2$O (0.4 mL), and the mixture was stirred at –10° C. for 30 minutes. The mixture was basified (pH 7–8) with aqueous 11 M sodium hydroxide and extracted with diethyl ether. The diethyl ether phase was dried (MgSO$_4$) and evaporated to give an oil, which was chromatographed on silica (toluene-ethyl acetate-triethylamine 7:2:1). The product was dissolved in diethyl ether and hydrogen chloride in diethyl ether was added. The precipitate was filtered to give (0.07 g, 0.18 mmol, 24%) of light-brown crystals. IR (KBr) 2111 (N$_3$) cm$^{-1}$; $^1$H NMR (CD$_3$OD) δ1.29 (m, 12H), 2.50 (m, 2H), 3.04 (m, 2H), 3.68 (m, 2H), 4.40 (t, 1H), 6.68 (s, 1H), 6.81 (m, 2H), 7.23 (m, 1H), 7.35 (m, 4H); mp. 131–134° C.; [α]$_D$–5.0° (c=0.1, methanol).

The starting compound (R)-N,N-diisopropyl-3-(5-amino-2-hydroxyphenyl)-3-phenylpropanamine was prepared as follows:

28.1 (R)-N,N-diisopropyl-3-(2-hydroxyphenyl)-3-phenylpropanamine

A solution of (R)-N,N-diisopropyl-3-(2-benzyloxy-5-bromophenyl)-3-phenylpropanamine (prepared as described in WO 94/11337, Example 1) (7.30 g, 15.2 mmol) treated as described in Example 1.3 above. Yield 4.47 g (94%).

28.2 (R)-N,N-Diisopropyl-3-[2-hydroxy-5-(4-methylphenylazo)phenyl]-3-phenylpropanamine NaNO$_2$ (0.27 g, 4.30 mmol) was added to a mixture of hydrochloric acid (0.64 mL, 7.70 mmol, conc.) and p-methylaniline (0.41 g, 3.80 mmol) in ice-water (20 mL). The mixture was stirred at 0° C. for 10 min. and then added to an ice-cold solution of (R)-N,N-diisopropyl-3-(2-hydroxyphenyl)-3-phenylpropanamine (1.00 g, 3.21 mmol) in THF (3 mL), H$_2$O (12 mL) and sodium hydroxide (0.69 g, 17.32 mmol). After stirring the mixture for 20 minutes, it was extracted with toluene, dried (MgSO$_4$), and evaporated to give an oil, which was chromatographed on (toluene-ethyl acetate-triethylamine 8:1:1) to give 0.83 g, 1.93 mmol, (60%) of the title compound. $^1$H NMR (CDCl$_3$) δ1.12 (d, 6H), 1.19 (d, 6H), 2.22 (m, 1H), 2.43 (m, 5H), 2.79 (m, 1H), 3.32 (m, 2H), 4.57 (d, 1H), 6.98 (d, 1H), 7.24 (m, 3H), 7.36 (m, 4H), 7.66 (m, 4H).

28.3 (R)-N,N-Diisopropyl-3-(5-amino-2-hydroxyphenyl)-3-phenylpropanamine

A solution of Na$_2$S$_2$O$_4$ (1.23 g, 12.8 mmol) in water (10 mL) was added to a solution of (R)-N,N-diisopropyl-3-[2-hydroxy-5-(4-methylphenylazo)phenyl]-3-phenylpropanamine (0.55 g, 1.28 mmol) in ethanol (50 mL) at 75° C. during 15 min. More dry Na$_2$S$_2$O$_4$ (1.23 g, 12.8 mmol) was added in 10 portions. Water was added to the solution which was then extracted with diethyl ether. The organic layer was dried (MgSO$_4$) and evaporated to give an oil, which was chromatographed on silica (n-hexane-ethanol-triethylamine 7:3:1) to give an oil. The product was dissolved in ethanol and hydrogen chloride in diethyl ether was added. The solvent was evaporated, redissolved in water and vacuum-dried wich yielded 0.25 g (60%).

EXAMPLE 29

(R) -N,N-Diisopropyl-3-[2-hydroxy-5-(3-hydroxypropyl)phenyl]-3-phenylpropanamine hydrochloride A solution of (R)-N,N-diisopropyl-3-[5-(2-ethoxycarbonylethyl)-2-hydroxyphenyl]-3-phenylpropanamine (2.0 g, 4.86 mmol) in THF (50 mL) was added dropwise to LAH (0.28 g, 7.29 mmol). After stirring for 2 h, the reaction was quenched and the solvent evaporated. The residue was recrystallized from ethanol-water. The product was dissolved in ethanol and hydrogen chloride in diethyl ether was added. White crystals were filtered off to give 0.82 g (46%); mp. 204–207° C.; [α]$_D$+12.8° (c=1.0, methanol); $^1$H NMR (DMSO) δ1.18 (t, 6H), 1.24 (t, 6H), 1.63 (m, 2H), 2.47 (m, 4H), 2.87 (br, 2H), 3.38 (q, 2H), 3.57 (br, 2H), 4.32 (t, 1H), 4.42 (t, 1H), 6.74 (d, 1H), 6.83 (d, 1H), 7.03 (s, 1H), 7.17 (t, 1H), 7.30 (m, 4H) Anal. (C$_{24}$H$_{35}$NO$_2$*1.0 HCl ) C, H, N.

The starting compound (R)-N,N-diisopropyl-3-[5-(2-ethoxycarbonylethyl)-2-hydroxyphenyl)-3-phenylpropanamine was prepared as follows:

29.1 (R)-N,N-Diisopropyl-3-[2-benzyloxy-5-(2-ethoxycarbonylethyl)phenyl]-3-phenylpropanamine A solution of triethyl phosphonoacetate (6.93 mL, 34.92 mmol) in THF (50 mL) was added dropwise to NaH (0.84 g, 29.10 mmol, 80%). The mixture was cooled to 0° C. and (R)-N,N-diisopropyl-3-(2-benzyloxy-5-formylphenyl)-3-phenylpropanamine, prepared as described in Example 17.1, (5.00 g, 11.64 mmol) in THF (50 mL) was added dropwise. The mixture was stirred for 3 h at 0° C. The solvent was evaporated and the residue was redissolved in toluene and washed twice with water. The organic layer was dried ($MgSO_4$) and the solvent evaporated to give 5.0 g (86%).

29.2 (R)-N,N-Diisopropyl-3-[5-(2-ethoxycarbonylethyl)-2-hydroxyphenyl]-3-phenylpropanamine (R)-N,N-Diisopropyl-3-12-benzyloxy-5-(2-ethoxycarbonylethyl)phenyl]-3-phenylpropanamine (3.0 g, 5.98 mmol) was treated as described in Example 1.3. Yield 2.0 g (81%); $^1$H NMR ($CDCl_3$) δ1.08 (d, 6H), 1.12 (d, 6H), 1.18 (t, 3H), 2.05 (m, 2H), 2.37 (m, 4H), 2.72 (t, 2H), 3.22 (m, 2H), 4.03 (q, 2H), 4.48 (m, 1H), 6.55 (s, 1H), 6.86 (m, 2H), 7.28 (m, 5H).

EXAMPLE 30

N,N-Diisopropyl-3-(5-ethylaminomethyl-2-hydroxyphenyl)-3-phenylpropanamine (R)-N,N-Diisopropyl-3-(5-formyl-2-hydroxyphenyl)-3-phenylpropanamine (prepared in Example 7.1) (1.23 g, 3.62 mmol) was dissolved in methanol (20 mL). Ethylamine [3.62 mL, 21.7 mmol (6M hydrochloric acid in methanol)] and sodium cyanoborohydride (0.14 g, 2.17 mmol) were added. The mixture was stirred overnight at room temperature. The solvent was evaporated and the residue was chromatographed on silica (toluene-ethyl acetate-triethylamine 7:3:1). The product was dissolved in diethyl ether and hydrogen chloride in diethyl ether was added. The resulting oil was stirred in diethyl ether over night to give crystals. Yield 0.70 g (44%); mp. 140–142° C.; $[\alpha]_D$ –5.0° (c=0.5, methanol); $^1$H NMR ($CD_3OD$) δ1.30 (m, 15H), 2.59 (m, 2H), 3.05 (m, 4H), 3.70 (m, 2H), 4.07 (s, 2H), 4.42 (t, 1H), 6.85 (d, 1H), 7.20 (m, 2H), 7.30 (t, 2H), 7.41 (d, 2H), 7.50 (s, 1H) Anal. ($C_{24}H_{36}N_2O$*2.0 HCl*0.5$H_2O$) C,H,N.

EXAMPLE 31

N-Cyclobutyl-N-methyl-3-(2-hydroxyphenyl)-3-phenylpropanamine hydrochloride

A solution of N-cyclobutyl-N-methyl-3-(2-benzyloxy-5-bromophenyl)-3-phenylpropanamine (1.60 g, 3.44 mmol) was hydrogenated over Pd/C (160 mg, 10%) in acetic acid at room temperature overnight. The solution was basified with sodium hydroxide (11 M) and the mixture was filtered. The filtrate was extracted with ethyl acetate, dried ($MgSO_4$) and the solvent evaporated. The residue was chromatographed on silica (toluen-triethylamine 9:1). The free amine was dissolved in diethyl ether and hydrogen chloride in diethyl ether was added to give an oil. The oil was crystallised in 2-propanol to give 0.90 g (79%); mp. 153–155° C.; $^1$H NMR ($CD_3OD$) δ1.78 (m, 2H), 2.22 (m, 4H), 2.48 (m, 2H), 2.72 (s, 3H), 2.95 (br, 2H), 3.68 (m, 1H), 4.44 (t, 1H), 6.78 (t, 1H), 6.79 (d, 1H), 7.03 (t, 1H), 7.12 (d, 1H), 7.18 (t, 1H), 7.28 (t, 2H), 7.34 (d, 2H); Anal. ($C_{20}H_{25}NO$*1.0 HCl*0.3 2-propanol) C, H, N.

The starting compound N-cyclobutyl-N-methyl-3-(2-benzyloxy-5-bromophenyl)-3-phenylpropanamine was prepared as follows:

31.1 N-Cyclobutyl-3-(2-benzyloxy-5-bromophenyl)-3-phenylpropanamine

5 M HCl-methanol (3.50 mL, 17.71 mmol) was added to a solution of cyclobutylamine (4.50 mL, 53.15 mmol) in methanol (14 mL). The mixture was added to 3-(2-benzyloxy-5-bromophenyl)-3-phenylpropanal (Example 20.1), (3.50 g, 8.86 mmol), followed by sodium cyanoborohydride (0.389 g, 6.20 mmol). The reaction mixture was stirred at room temperature overnight. The solvent was evaporated and the residue was chromatographed on silica (toluene-ethyl acetate-triethylamine 92:4:4). Yield 2.61 g (65%); $^1$H NMR ($CDCl_3$) δ1.57 (m, 5H), 2.14 (m, 4H), 2.47 (t, 2H), 3.16 (m, 1H), 4.45 (t, 1H), 5.00 (s, 2H), 6.75 (d, 1H), 7.10–7.47 (m, 12H).

31.2 N-Cyclobutyl-N-methyl-3-(2-benzyloxy-5-bromophenyl)-3-phenylpropanamine 5 M HCl-methanol (0.46 mL, 2.32 mmol), formaldehyde (0.870 g, 28.97 mmol) and sodium cyanoborohydride (0.255 g, 4.056 mmol) were added to a solution of N-cyclobutyl-3-(2-benzyloxy-5-bromophenyl)-3-phenylpropanamine (2.61 g, 5.79 mmol) in methanol (8 mL). The reaction mixture was stirred at room temperature overnight. The solvent was evaporated and the residue was chromatographed on silica (hexane-triethylamine, 9:1). Yield 1.59 g (59%); $^1$H NMR ($CDCl_3$) δ1.59 (m, 2H), 1.73 (m, 2H), 1.91 (m, 2H), 2.06 (s, 3H), 2.16 (m, 4H), 2.68 (m, 1H), 4.38 (t, 1H), 5.00 (s, 2H), 6.72 (d, IH), 7.12–7.58 (m, 12H).

EXAMPLE 32

N-Cyclopentyl-N-methyl-3-(2-hydroxyphenyl)-3-phenylpropanamine hydrochloride N-Cyclopentyl-N-methyl-3-(2-benzyloxy-5-bromophenyl)-3-phenylpropanamine (2.46 g, 5.14 mmol) was treated as described in Example 31. The crude was not chromatographed but crystallised from aqueous ethanol. Yield 1.24 g (70%) $^1$H NMR (DMSO) δ1.48 (br, 1H), 1.66 (br, 2H), 1.85 (br, 1H), 2.46 (br, 2H), 2.68 (s, 3H), 2.87 (br, 2H), 3.53 (m, 1H), 4.35 (t, 1H), 6.77 (t, 1H), 6.83 (d, 1H), 7.01 (t, 1H), 7.16 (t, 1H), 7.27 (t, 3H), 7.33 (d, 2H), 9.57 (br, 1H), 10.85 (br, 1H); mp 169–172° C.; Anal. ($C_{21}H_{27}NO$*HCl) C, H, N.

The starting compound N-cyclopentyl-N-methyl-3-(2-benzyloxy-5-bromophenyl)-3-phenylpropanamine was prepared as follows:

32.1 N-Cyclopentyl-3-(2-benzyloxy-5-bromophenyl)-3-phenylpropanamine 3-(2-Benzyloxy-5-bromophenyl)-3-phenylpropanal, prepared as described in Example 20.1, (7.00 g, 17.71 mmol) was treated with cyclopentylamine as described in Example 31.1. Yield 4.9 g (59%); $^1$H NMR ($CDCl_3$) δ1.20 (m, 2H), 1.40–1.80 (m, 6H), 2.18 (m, 2H), 2.55 (t, 2H), 2.98 (m, 1H), 4.45 (t, 1H), 5.00 (s, 2H), 6.75 (d, 1H), 7.10–7.45 (m, 12H).

32.2 N-Cyclopenthyl-N-methyl-3-(2-benzyloxy-5-bromophenyl)-3-phenylpropanamine A solution of N-cyclopentyl-3-(2-benzyloxy-5-bromophenyl)-3-phenylpropanamine (3.50 g, 7.53 mmol) was treated as described in Example 31.2. Yield 2.46 g (68%); $^1$H NMR ($CDCl_3$) δ1.10–1.80 (m, 8H), 2.19 (m, 5H), 2.36 (m, 2H), 2.58 (m, 1H), 4.37 (t, 1H), 4.98 (s, 2H), 6.72 (d, 1H), 7.10–7.50 (m, 12H).

EXAMPLE 33

N,N-Diisopropyl-3-(2-aminophenyl)-3-phenylpropanamine hydrochloride

LAH (0.94 g, 24.8 mmol) was added to a solution of N,N-diisopropyl-3-(2-aminophenyl)-3- phenylpropenylamide (1.6 g, 4.98 mmol) in THF (90 mL). The mixture was stirred for 72 h at room temperature. The reaction was quenched and the solvent evaporated. The crude residue was fractionated on a reversed-phase PEP RPC HR 30/26 (Pharmacia Biotech AB, Sweden) column using 20 % acetonitrile with 0.1% TFA. Hydrochloric acid was added to the pure fractions and the solvent was evaporated. The residue was redissolved in water and freeze-dried giving 88 mg (5%); mp 138–142° C.; $^1$H NMR (DMSO) $\delta$1.25 (m, 12H), 2.47 (m, 1H), 2.65 (m, 1H), 2.87 (m, 1H), 3.13, (m, 1H), 3.59 (br, 2H), 4.58 (t, 1H), 7.20–7.37 (m, 5H), 7.42 (m, 2H), 7.54 (d, 2H), 9.94 (br, 2H). Anal. ($C_{21}H_{30}N_2*HCl*H_2O$) C, N, H: calcd.8.5; found 7.9.

The starting compound N,N-diisopropyl-3-(2-aminophenyl)-3-phenylpropenylamide was prepared as follows:

33.1 2-(3,5-Dimethyl-4-hydroxyphenylazo) benzophenone

A slurry of ice (500 mL), hydrochloric acid (16.8 mL, 202 mmol, conc.), 2-aminobenzophenone (20.00 g, 101 mmol) and $NaNO_2$ (9.0 g, 131 mmol) were added to a stirred solution of 2,6-dimethylphenol (18.40 g, 151 mmol) and sodium hydroxide (16.20 g, 404 mmol) in ice-cold water (100 mL). After 20 minutes the mixture was extracted with diethyl ether. The organic phase was washed with hydrochloric acid (6 M), $NaHCO_{3(aq)}$, dried ($MgSO_4$) and the solvent evaporated. The crude residue was chromatographed on silica (toluene) and pure fractions were pooled and evaporated to give a red oil. The oil was crystallised in hexane/toluene to give 7.73 g (23%).

33.2 2-(3,5-Dimethyl-4-tosyloxyphonylazo) benzophenone

A mixture of 2-(3,5-dimethyl-4-hydroxyphenylazo)-benzophenone (7.73 g, 23.41 mmol) and tosyl chloride (9.4 g, 49 mmol) in pyridine (20 mL) was stirred at 90° C. for 9 h. Water was added and the mixture was extracted with diethyl ether. The organic phase was washed with sodium hydroxide (2 M) and hydrochloric acid (2 M), dried ($MgSO_4$) and the solvent evaporated. The product was crystallised in ethanol to give 7.62 g (67%); $^1$H NMR ($CDCl_3$) $\delta$2.08 (s, 6H), 2.49 (s, 3H), 7.05 (s, 2H), 7.37 (m, 4H), 7.48 (m, 1H), 7.62 (m, 3H), 7.82 (m, 5H).

33.3 N,N-Diisopropyl-3-[2-(3,5-dimethyl-4-tosyloxyphenyl-azo)phenyl]-3-3-phenylpropenamide 2-(3,5-Dimethyl-4-tosyloxyphenylazo)benzophenone (7.22 g, 14.9 mmol) was treated as described in Example 4.2 but with 3 eq of N,N-diisopropylacetamide diethylphosphonate and sodium hydride. Yield 4.5 g (50%). $^1$H NMR ($CDCl_3$) $\delta$0.72 (d, 3H), 0.82 (br, 3H), 1.28 (d, 3H), 1.42 (d, 3H), 2.10 (s, 3H), 2.14 (s, 3H), 2.45 (s, 3H), 3.25 (m, 1H), 4.28 (m, 1H), 6.05 and 6.63 (s, 1H), 7.00–7.90 (m, 15H).

33.4 N,N-Diisopropyl-3-[2-(3,5-dimethyl-4-hydroxyphenylazo)phenyl]-3-phenylpropenamide A solution of potassium hydroxide (10.3 mL, 6 M) and N,N-diisopropyl-3-[2-(3,5-dimethyl-4-tosyloxyphenylazo) phenyl]-3-phenylpropenamide (3.5 g, 5.74 mmol) in ethanol (110 mL) was refluxed for 1 h. The mixture was acidified with hydrochloric acid (conc.) and the solvent evaporated. The residue was partioned between toluene and water. The organic layer was dried ($MgSO_4$) and the solvent evaporated. The crude residue was chromatographed on silica (toluene-ethyl acetate 9:2). Yield 1.3 g (50%). 1H NNR ($CDCl_3$) $\delta$0.71 (d, 3H), 0.80 (br, 3H), 1.27 (d, 3H), 1.40 (d, 3H), 2.20 (s, 3H), 2.23 (s, 3H), 3.25 (m, 1H), 4.35 (m, 1H), 5.52 (brd, 1H), 6.05 and 6.60 (s, 1H), 7.00–7.80 (m, 11H).

33.5 N,N-Diisopropyl-3-(2-aminophenyl)-3-phenylpropenamide

N,N-Diisopropyl-3-[2-(3,5-dimethyl-4-hydroxyphenylazo)phenyl]-3-phenylpropenamide (2.58 g, 5.68 mmol) was treated as described in Example 28.3. The crude residue gave crystals from aqueous ethanol. Yield 1.23g (67%).

EXAMPLE 34

N,N-Diisopropyl-3-(benzoxazol-2-yl)-3-phenylpropanamine, hydrochloride

A mixture of N,N-diisopropyl-3-ethoxycarbonyl-3-phenylpropanamine (2.51 g, 8.6 mmol), 75% aqueous ethanol (15 mL) and 2 M NaOH (8.5 mL, 17 mmol) was refluxed over night. After evaporation of the solvent, the residue was made acidic with 2 M HCl and the solvent was evaporated. A mixture of the residual semicrystalline oil was heated with o-aminophenol (1.8 g, 16.5 mmol) and polyphosphoric acid (12 g) at 200° C. for 2 hours under $N_2$. The somewhat cooled hard solid was dissolved in water and washed once with diethyl ether. The aqueous phase was made alkaline (11 M NaOH) and extracted twice with diethyl ether. The combined organic phases were dried ($Na_2SO_4$) and the solvent evaporated. The crude product was chromatographed on silica (petroleum ether/triethylamine 97:3). The pure amine was precipitated as hydrochloride from diethyl ether affording white crystals, 1.27 g (39%): mp 197–198° C.; $^1$H NMR ($CDCl_3$) $\delta$1.49 (m, 12H), 2.80–3.20 (m, 4H), 3.48 (br, 2H), 4.45 (t, 1H), 7.25–7.48 (m, 8H), 7.70 (m, 1H), 11.48 (br, 1H).

The starting compound N,N-diisopropyl-3-ethoxycarbonyl-3-phenylpropanamine was prepared as follows:

34.1 N,N-Diisopropyl-3-cyano-3-phenylpropanamine

Sodium hydride, 80% in mineral oil (2.82 g, 94 mmol), was washed with petroleum ether and dried under a $N_2$-stream. Dry DMF (100 mL) was added. Benzyl cyanide (12.1 g, 103 mmol) was added to the stirred suspension over a period of 20 min. The temperature rose to approx. 45° C. The mixture was stirred for another 15 min. 2-Chloroethyl-diisopropylamine (15.4 g, 94 mmol) was added. All the amine was consumed within 30 min. Most of the DMF was evaporated under reduced pressure and the residue was dissolved in water/diethyl ether. The aqueous phase was extracted once with diethyl ether and the combined organic phases were extracted twice with 2 M HCl. The combined aqueous phases were made alkaline (11 M NaOH) and extracted twice with diethyl ether. The combined organic phases were then dried ($Na_2SO_4$) and the solvent was evaporated. The crude product was chromatographed on silica (petroleum ether-triethylamine, 40:1), affording the title compound, 16.8 g (67%), as a colourless liquid. $^1$H NMR ($CDCl_3$) $\delta$1.01 (m, 12H), 1.97 (m, 2H), 2.62 (m, 2H), 3.00 (m, 2H), 4.02 (dd, 1H), 7.17–7.40 (m, 5H).

34.2 N,N-Diisopropyl-3-carbamoyl-3-phenylpropanamine

N,N-Diisopropyl-3-cyano-3-phenylpropanamine (11.6 g, 47.5 mmol) was mixed with $H_2SO_4$ (90%, 100 mL) and the mixture was stirred at 100° C. for 30 min. The reaction mixture was poured on ice, made alkaline (11 M NaOH) and extracted twice with diethyl ether. The combined organic phases were dried ($Na_2SO_4$) and the solvent evaporated, affording the title compound as a colourless oil, 12.4 g (100%); $^1$H NMR ($CDCl_3$) δ1.26 (m, 12H), 2.14 (m, 1H), 2.60 (m, 1H), 2.73 (t, 2H), 3.31 (m, 2H), 3.86 (t, 1H), 6.06 (br, 2H), 7.51–7.61 (m, 5H).

34.3 N,N-Diisopropyl-3-ethoxycarbonyl-3-phenylpropanamine

N,N-Diisopropyl-3-carbamyl-3-phenylpropanamine (26.5 g 0.100 mol) was added into aqueous ethanol (90%, 300 mL) containing conc. $HNO_3$ (13.3 g, 0.21 mol) and refluxed for five days. Most of the solvent was evaporated under reduced pressure and the residue was mixed with water/diethyl ether. The organic phase was washed once with water. The combined aqueous phases were made alkaline (11 M NaOH) and extracted twice with diethyl ether. The combined organic phases were then dried ($Na_2SO_4$) and the solvent evaporated. The crude product was chromatographed on silica (petroleum ether-triethylamine, 97/3), to afford the title compound as a colourless liquid, 20.1 g (68.7%): $^1$H NMR ($CDCl_3$) δ0.96 (m, 12H), 1.21 (t, 3H), 1.81 (m, 1H), 2.22 (m, 1H), 2.40 (t, 2H), 3.66 (dd, 1H), 4.12 (m, 2H), 7.20–7.32 (m, 5H).

EXAMPLE 35

N,N-Diisopropyl-3-(oxazol-5-yl)-3-phenylpropanamine hydrochloride

Freshly distilled methylisonitrile (1.66 g, 40.4 mmol) was dissolved in dry THF (75 mL) under $N_2$-atmosphere and the mixture was cooled to −78° C. 1.4 M n-BuLi (29 mL, 40.5 mmol) was slowly added to the solution, followed by N,N-diisopropyl-3-ethoxycarbonyl-3-phenylpropanamine (4.71 g, 16.2 mmol) in THF (10 mL). The reaction temperature was allowed to rise to −20° C., at which the reaction was quenched with HOAc (10 mL). The solvent was evaporated and the residue was mixed with diethyl ether/water. The organic phase was washed once with water and the combined aqueous phases were made alkaline with 11 M NaOH and extracted twice with diethyl ether. The organic phases were put together, dried ($Na_2SO_4$) and the solvent evaporated. The crude product was chromatographed on silica (chloroform-methanol-conc. ammonia, 490:10:1). The pure amine was precipitated with HCl-saturated diethyl ether, affording the title compound as a glassy oil, 1.4 g (48%). $^1$H NMR ($CD_3OD$) δ1.21–1.40 (m, 12H), 2.57 (m, 1H), 2.68 (m, 1H), 2.91 (m, 1H), 3.23 (m, 1H), 3.72 (m, 2H), 4.41 (dd, 1H), 7.39 (m, 5H), 7.52 (s, 1H), 9.13(s, 1H).

EXAMPLE 36

N,N-Diisopropyl-3-(imidazol-4(5)-yl)-3-phenylpropanamine dihydrochloride

N,N-Diisopropyl-3-oxazol-5-yl-3-phenylpropanamide (0.76 g 2.6 mmol) was mixed with formamide (5 mL). The mixture was heated at 175° C. for 6 hours. The solvent was evaporated under vacuum (1 mm Hg) and the residue was partitioned between 1 M HCl and diethyl ether. The aqueous phase was made alkaline (11 M NaOH) and extracted twice with diethyl ether. The combined organic phases were dried ($Na_2SO_4$) and the solvent evaporated. The light brown oil was dissolved in diethyl ether and added to a suspension of lithium aluminium hydride (LAH) (0.70 g, 5.4 mmol) in diethyl ether. The reaction mixture was stirred at ambient temperature overnight. The reaction was quenched, and the solvent was evaporated. The crude amine was dissolved in EtOAc and precipitated as a hydrochloride salt with HCl-saturated diethyl ether to afford the title compound as hygroscopic crystals, 0.32 g (35%): $^1$H NMR ($CDCl_3$) δ1.38 (m, 12H), 2.80 (m, 2H), 3.00 (m, 1H), 3.16 (m, 1H), 3.64 (br, 2H), 4.41 (m, 1H), 6.89 (s, 1H), 7.27–7.41 (m, 5H), 8.78 (s, 1H), 10.32 (br, 2H).

The starting compound N,N-diisopropyl-3-oxazol-5-yl-3-phenylpropanamide (0.76 g 2.6 mmol) was prepared as follows:

36.1 3-Cyano-3-phenylpropanoic acid

Ethyl cinnamate (85.3 g, 0.484 mol), potassium cyanide (64.2 g, 0.986 mol) and ammonium chloride (38.9 g, 0.726 mol) were mixed with aqueous DMF (90%, 360 mL). The mixture was stirred at 105° C. for 7 hours. The somewhat cooled mixture was filtered and most of the DMF was evaporated. The residue was taken up in diethyl ether and 1 M HCl. The aqueous phase was extracted twice with diethyl ether. The combined diethyl ether phases were evaporated and the black oil was suspended in EtOH (200 mL) and 2 M NaOH (250 mL) and stirred at ambient temperature for 2 hours. The mixture was diluted with brine (200 mL) and water (400 mL) and washed twice with diethyl ether. After acidification (12 M HCl) the aqueous phase was extracted three times with diethyl ether. The pooled organic phases were dried ($Na_2SO_4$) and the solvent evaporated affording the title compound as a black oil, 74 g (87%): $^1$H NMR ($CDCl_3$) δ1.05 (d, 3H), 1.17 (d, 3H), 1.22 (d, 6H), 2.68 (dd, 1H), 3.16 (dd, 1H), 3.4 (br, 1H), 3.76 (m, 1H) 4.19 (dd, 1H), 7.31 (m, 5H), 8.9 (br, 1H).

36.2 N,N-Diisopropyl-3-cyano-3-phenylpropanamide

3-Cyano-3-phenylpropanoic acid (67.7 g, 0.389 mol) was dissolved in 2-PrOH. To the filtered acid solution was carefully added KOH (18.4 g, 0.33 mol) dissolved in 2-PrOH (200 mL), diethyl ether (100 mL) was added and the precipitate was filtered off. The dried acid salt (51.9 g, 0.24 mol) was suspended in benzene (400 mL) and oxalyl chloride was carefully added. The reaction mixture was stirred at 80° C. for 2 hours. The solvent was evaporated and the residue was co-evaporated twice with benzene. The brown oil was dissolved in benzene (200 mL) and cooled in an ice-bath. A solution of diisopropylamine (82 g, 0.81 mol) in benzene (200 mL) was added to the stirred reaction mixture during 45 min. The mixture was left to slowly warm up to room temperature overnight. The solvent was evaporated and the residue was taken up in diethyl ether and 1 M HCl. The organic phase was washed once with water, once with 1 M NaOH, again with water, dried ($Na_2SO_4$) and the solvent evaporated to afford the title compound as a dark brown oil, 41.7 g (41%): $^1$H NMR ($CDCl_3$) δ1.07 (d, 3H), 1.17 (d, 3H), 1.36 (m, 6H), 2.77 (m, 1H), 2.97 (m, 1H), 3,51 (br, 1H), 3.81 (m, 1H), 4.50 (dd, 1H), 7.39 (m, 5H).

36.3 N,N-Diisopropyl-3-carbamoyl-3-phenylpropanamide

N,N-Diisopropyl-3-cyano-3-phenylpropanamide (21.1 g, 82 mmol) was dissolved in EtOH (130 mL) and 2 M NaOH (100 mL). Hydrogen peroxide (30%, 20.2 mL, 200 mmol) was added and the mixture was stirred at ambient temperature for two hours. The resulting precipitate was filtered, washed with water and dried, yielding the title compound as white crystals, 15.6 g (69%): $^1$H NMR (CDCl$_3$) δ1.09 (d, 3H), 1.19 (d, 3H), 1.31 (m, 6H), 2.51 (dd, 1H), 3.30 (dd, 1H), 3.41 (m, 1H), 4.02 (m, 1H), 4.18 (dd, 1H), 5.7 (br, 1H), 6.4 (br, 1H), 7.21–7.42 (m, 5H).

36.4 N,N-Diisopropyl-3-ethoxycarbonyl-3-phenylpropanamide

N,N-Diisopropyl-3-carbamoyl-3-phenylpropanamide was treated as described in Example 34:3 (two days of reflux and no chromatography) which gave the title compound as a colourless semicrystalline oil, 15.9 g (93%): $^1$H NMR (CDCl$_3$) δ1.19 (m, 9H), 1.36 (m, 6H), 2.53 (dd, 1H), 3.18 (dd, 1H), 3.4 (br, 1H), 3.98 (m, 1H), 4.15 (m, 3H), 7.31 (m, 5H).

36.5 N,N-Diisopropyl-3-oxazol-5-yl-3-phenylpropanamide

The method described for Example 35 above was used, starting from N,N-diisopropyl-3-ethoxycarbonyl-3-phenylpropanamide. The crude was chromatographed on silica (petroleum ether-EtOAc, 3:2), affording the title compound as a light yellow oil, 0.77 g (46%): $^1$H NMR (CDCl$_3$) δ1.00 (d, 3H), 1.14 (d, 3H), 1.29 (m, 6H), 2.98 (m, 2H), 3.4 (br, 1H), 3,93 (m, 1H), 4.79 (t, 1H), 6.82 (s, 1H), 7.28 (m, 5H), 7.76 (s, 1H).

EXAMPLE 37

N,N-Diisopropyl-3-(oxazol-2-yl)-3-phenylpropanamine hydrochloride

A mixture of N,N-diisopropyl-3-carbamoyl-3-phenylpropanamine, prepared in Example 34.2 (4.05 g, 15.4 mmol), 1,2-dichloroethyl ethyl ether (2,32 g, 16.2 mmol), water (0.300 g, 16.6 mmol) and formic acid (50 mL) was stirred at 75° C. for 3 hours. The formic acid was evaporated and the residue was dissolved in water/diethyl ether. The aqueous phase was made alkaline (11 M NaOH) and extracted twice with diethyl ether. The combined organic phases were dried (Na$_2$SO$_4$) and the solvent evaporated. The crude product was chromatographed on silica (petroleum ether-triethylamine 97:3). The pure amine was precipitated as hydrochloride salt with HCl-saturated diethyl ether, affording the title compound as white crystals, 0.61 g (12%): mp 157–158° C.; $^1$H NMR (DMSO(d$_6$)) δ1.11 (m, 12H), 2.35 (m, 1H), 2.63 (m, 1H), 3.03 (m, 2H), 3.56 (m, 2H), 4.45 (m, 1H), 7.21–7.40 (m, 6H) 8.06 (d, 1H), 10.20 (br, 1H).

EXAMPLE 38

N,N-Diisopropyl-3-phenyl-3-(thiazol-2-yl) propanamine hydrochloride

The title compound was prepared in an analogous manner to that described in Example 37. N,N-Diisopropyl-3-phenyl-3-thiocarbamoylpropanamine (1.11 g, 4.0 mmol) yielded white crystals of the title compound, 1.12 g (82%): mp 155–156° C.; $^1$H NMR (CDCl$_3$) δ1.37 (m, 12H), 2.75–3.15 (m, 4H), 3.60 (m, 2H), 4.45 (t, 1H), 7.25–7.36 (m, 6H), 7.71 (d, 1H), 11.30 (br, 1H).

The starting compound N,N-diisopropyl-3-phenyl-3-thiocarbamoylpropanamine was prepared as follows:

38.1 N,N-Diisopropyl-3-phenyl-3-thiocarbamoylpropanamine

H$_2$S was bubbled into a solution of N,N-diisopropyl-3-cyano-3-phenylpropanamine, prepared in Example 34.1, (3.45 g, 14.3 mmol) and triethylamine (2.0 g, 20 mmol) in dry pyridine (10 mL) until saturation was achieved. The stirred reaction was held under H$_2$S-atmosphere at 65° C. for 5 days. The pyridine was evaporated and the crude product was chromatographed on silica (chloroform-methanol-conc. ammonia 380:20:1), yielding the title compound as a colourless glassy oil, 3.1 g (78%): $^1$H NMR (CDCl$_3$) δ0.99 (m, 12H), 2.07 (m, 1H), 2.40 (m, 3H), 3.05 (m, 2H), 4.10 (t, 1H), 7.20–7.45 (m 5H), 7.7–8.1 (b, 1H), 8.0–8.5 (br, 1H).

EXAMPLE 39

N,N-Diisopropyl-3-(4-methylthiazol-2-yl)-3-phenyl-propanamine hydrochloride

The title compound was prepared in an analogous manner to that described in Example 37. N,N-Diisopropyl-3-phenyl-3-thiocarbamoylpropanamine, prepared in Example 38.1, (1.5 g, 5,4 mmol), and 2-chloroacetone (0.75 g, 8.1 mmol) yielded the title compound as a white amorphous substance, 1.1 g (56%): mp 178–181° C.; $^1$H NMR (CDCl$_3$) δ1.44 (m, 12H), 2.50 (s, 3H), 2.98 (m, 3H), 3.18 (m, 1H), 3.60 (m, 2H), 6.94 (d, 1H), 7.30–7.47 (m, 5H), 11.15 (br, 1H).

EXAMPLE 40

N,N-Diisopropyl-3-(thiazol-5-yl)-3-phenylpropanamine hydrochloride

The title compound was prepared in an analogous manner to that described in Example 35. Reaction with N,N-diisopropylamine-3-ethoxythiocarbonyl-3-phenylpropanamine (1.14 g, 3.7 mmol) gave a crude that was chromatographed on silica (petroleum ether-triethylamine 97:3), affording white crystals of the title compound, 0.19 g (30%): mp 193–194° C.; $^1$H NMR (CDCl$_3$) δ1.1.34 (m, 12H), 2.85 (m, 4H), 5.56 (m, 2H), 4.29 (t, 1H), 7.26–7.39 (m, 5H), 7.73 (s, 1H), 8.71 (s, 1H) 11.61 (br, 1H).

The starting compound N,N-diisopropylamine-3-ethoxythiocarbonyl-3-phenylpropanamine was prepared as follows:

40.1 N,N-Diisopropyl-3-ethoxythiocarbonyl-3-phenyl-propanamine

HCl-gas was bubbled through an ice-cold solution of N,N-diisopropyl-3-cyano-3-phenylpropanamine (2.9 g, 12 mmol), prepared in Example 34.1, in dried ethanol (50 mL, molecular sieve 3 Å) until saturation. The stirred reaction was held under HCl-atmosphere at room temperature overnight. The solvent was carefully evaporated and the remaining oil was dissolved in dry pyridine (100 mL). To this solution was added triethylamine (5.7 g, 56 mmol) and to the now thick suspension was bubbled H$_2$S until saturation was achieved. The dark olive-green reaction mixture was held under a H$_2$S-atmosphere at 65° C. overnight. The solvent was evaporated and the residue was partioned between 1 M HCl and diethyl ether. The aqueous phase was made alkaline (11 M NaOH) and extracted twice with diethyl ether. The combined organic phases were dried (Na$_2$SO$_4$) and the solvent evaporated. The crude product was chromatographed on silica (chloroform-methanol-conc. ammonia, 198:1:1), affording the title compound as a straw-coloured liquid, 1.24 g (33%): $^1$H NMR (CDCl$_3$) δ0.95 (m, 12H), 1.34 (t, 2H), 1.97 (m, 1H), 2.37 (m, 3H), 2.98 (m, 2H), 4.10 (t, 1H) 4.46 (m, 2H), 7.13–7.39 (m, 5H).

EXAMPLE 41

N,N-Diisopropyl-3-(2-hydroxyphenyl)-3-(2-thienyl)-propanamine fumarate

To a suspension of lithium aluminium hydride (LAH) (0.51 g 13.3 mmol) in THF (30 mL), N,N-diisopropyl-3-(2- hydroxyphenyl)-3-(2-thienyl)propanamide (2.0 g, 5.33 mmol) was added and warmed to 50° C. overnight. The reaction mixture was quenched and the solvent was evaporated. The residue was dissolved in diethyl ether and extracted twice with 2 M HCl, and the combined aqueous phases were washed twice with diethyl ether. The aqueous phase was made alkaline (11 M NaOH) and extracted three times with diethyl ether, the combined organic phases were washed once with brine, dried ($MgSO_4$) and the solvent evaporated. The pure amine was crystallised from methanol as its fumarate, yielding the title compound as white crystals, 1.52 g (58%): mp 203–205° C.; $^1$H NMR (DMSO) δ1.00 (d, 12H), 2.02 (q, 2H), 2.33 (m, 2H), 3.18 (m 2H), 4,62 (t, 1H), 6.50 (s, 1H), 6.68–7.18 (m, 6H), 7.28 (t, 1H).

The starting compound N,N-diisopropyl-3-(2-hydroxyphenyl)-3-(2-thienyl)propanamide was prepared as follows:

41.1 N,N-Diisopropyl-3-(2-thienyl)propenamide

2-Bromothiophene (2.28 g, 14.0 mmol), N,N-diisopropylacrylamide (1.55 g, 10.0 mmol), palladium(II) acetate (34 mg, 0.15 mmol), tri-o-tolylphosphine (183 mg, 0.6 mmol), tri-n-butyl amine (2.04 g, 11.0 mmol) and dry DMF (5 mL) were mixed under a $N_2$-atmosphere. The mixture was heated to 130° C. for 9 hours. Diethyl ether and $H_2O$ was added to the somewhat cooled mixture. The aqueous phase was extracted twice with diethyl ether. The combined organic phases were washed twice with 2 M HCl, once with water, once with brine, and dried ($MgSO_4$), and the solvent was then evaporated. The crude product was chromatographed on silica (petroleum ether-ethyl acetate 4:1), affording a yellow oil, 1.58 g (66%): $^1$H NMR (CDCl$_3$) 67 1.35 (br, 12H), 3.9 (br, 1H), 4.1 (br 1H), 6.65 (d, 1H), 7.00–7.30 (m, 3H), 7.72 (d, 1H).

41.2 2-Methoxyphenyllithium

2-Methoxybromobenzene (8.44 g 45.1 mmol) was dissolved in dry diethyl ether (15 mL). The mixture was cooled to −78° C. n-BuLi (17.8 mL, 45.0 mmol) was added and the mixture was stirred for one hour at −78° C. and then for 20 min. at −10° C. The aryl lithium solution was used immediately.

41.3 N,N-Diisopropyl-3-(2-methoxyphenyl)-3-(2-thienyl)propanamide

Copper(I)bromide dimethyl sulfide complex (4.63 g 22.5 mmol) was dissolved in dimethyl sulfide (18 mL), and diethyl ether (15 mL). The solution was cooled to 0° C., whereafter 2-methoxyphenyllithium (41.2) (45 mmol) was added. After 10 min., the temperature was lowered to −78° C. Trimethylsilylchloride (4.89 g, 45.0 mmol) was added, followed by N,N-diisopropyl-3-(2-thienyl)propenamide (41.1) (3.56 g, 15 mmol) in diethyl ether (20 mL). The temperature was allowed to slowly rise to room temperature overnight. The reaction was quenched with saturated $NH_4Cl$ (10 mL) and conc. ammonia (10 mL). Diethyl ether (80 mL) was added and the mixture was filtered through Celite. The aqueous phase was extracted twice with diethyl ether. The combined organic phases were washed once with brine and dried ($MgSO_4$). The solvent was evaporated and the crude product was chromatographed on silica (petroleum ether-ethyl acetate 3:1), affording a yellow oil, 3.75 g (73%): $^1$H NMR (CDCl$_3$) d 1.12 (t, 6H), 1.29 (t, 6H), 3.02 (m, 2H), 3.4 (br, 1H), 3.80 (s, 3H), 4.03 (m, 1H), 5.26 (t, 1H), 6.8–7.3 (m, 7H).

41.4 N,N-Diisopropyl-3-(2-hydroxyphenyl)-3-(2-thienyl)propanamide

A solution of N,N-diisopropyl-3-(2-methoxyphenyl)-3-(2-thienyl)propanamide (2.37 g, 6.9 mmol) in dichloromethane(35 mL) was cooled down to −78° C. and boron tribromide (5.9 g 23.57 mmol) was added. The reaction mixture was allowed to slowly warm to room temperature. The reaction was quenched by slow addition of water (20 mL). The pH was adjusted to around 6 with $NaHCO_3$(s) and the mixture was extracted three times with $CH_2Cl_2$. The combined organic phases were washed once with brine, dried ($MgSO_4$) and the solvent was evaporated. This crude product (2.46 g, 107%) was used without further purification. $^1$H NMR (CDCl$_3$) δ1.05 (d, 3H), 1.20 (m, 6H), 1.35 (d, 3H), 3.16 (m, 2H), 3.4 (br, 1H), 4.0 (m, 1H), 5.24 (dd. 1H), 6.7–7.2 (m, 7H).

Examples 42–54 and 57 and 58 were prepared with the methodology described for Example 41, starting with the appropriate acrylamides and aryl bromides.

EXAMPLE 42

N,N-Diisopropyl-3-(2,4-dihydroxyphenyl)-3-(2-thienyl)propanamine

The crude product was crystallised from petroleum ether/ethyl acetate affording the title compound, 0.41 g as slightly pink crystals: mp 102–109° C.; $^1$H NMR (CDCl$_3$) δ1.11 (m, 12H), 2.01 (m, 1H), 2.41 (m, 2H), 2.72 (m, 1H), 3.26 (m, 2H), 4.66 (dd, 1H), 6.30 (dd, 1H), 6.45 (d, 1H), 6.73 (d, 1H), 6.91–7.00 (m, 2H), 7.17 (dd, 1H).

EXAMPLE 43

N,N-Diisopropylamine-3-(2-methoxyphenyl)-3-(2-thienyl)propanamine, fumarate White crystals, 0.95 g: mp 153–155° C.; $^1$H NMR (CD$_3$OD) δ1.28 (m, 12H), 2.48 (m, 2H), 3.05 (m, 2H), 3.68 (m, 2H), 3.85 (s, 3H), 4.71 (t, 1H), 6.68 (s, 2H), 6.89–7.03 (m, 4H), 7.20–7.30 (m, 3H).

EXAMPLE 44

N,N-Diisopropyl-3-(2,4-dimethoxyphenyl)-3-(2-thienyl)propanamine fumarate

White crystals, 1.52 g: mp 103–109° C.; $^1$H NMR (CD$_3$OD) δ1.28 (m, 12H), 2.46 (m, 2H), 3.04 (m, 2H), 3.66 (m, 2H), 3.77 (s, 3H), 3.82 (s, 3H), 4.60 (t, 1H), 6.46–6.58 (m, 2H), 6.68 (s, 2H), 6.91–6.97 (m, 2H), 7.09–7.26 (m, 2H).

EXAMPLE 45

N,N-Diisopropyl-3-(3-methoxyphenyl)-3-(2-thienyl) propanamine hydrochloride White crystals, 1.16 g: mp 95–97° C.; $^1$H NMR (CD$_3$OD) δ1.28 (d, 12H), 2.49 (m, 2H), 2.96 (m, 1H), 3.13 (m, 1H), 3.68 (m, 2H), 3.77 (s, 3H), 4.31 (t, 1H), 6.83 (m, 1H), 6.68–7.02 (m, 4H), 7.27 (m, 2H).

EXAMPLE 46

N,N-Diisopropyl-3-(4-methoxyphenyl)-3-(2-thienyl) propanamine hydrochloride White amorphous substance, 0.50 g: mp 157–160° C.; $^1$H NMR (CD$_3$OD) δ1.31 (m, 12H), 2.47 (m, 2H), 2.94 (m, 1H), 3.12 (m, 1H); 3.68 (br, 2H), 3.77 (s, 3H), 4.28 (t, 1H), 6.87–7.00 (m, 4H), 7.23–7.32 (m, 3H).

EXAMPLE 47

N-Isopropyl-N-methyl-3-(2-methoxyphenyl)-3-(2-thienyl)propanamine fumarate

White crystals, 1.32 g: mp 141–143° C.; $^1$H NMR (CD$_3$OD) δ1.24 (m, 6H), 2.50 (m, 2H), 2.73 (s, 3H), 3.04

(m, 2H), 3.58 (m, 1H), 3.84 (s, 3H), 4.73 (t, 1H), 6.68 (s, 2H), 6.96 (m, 4H), 7.24 (m, 3H).

EXAMPLE 48

N,N-Diisopropyl-3-phenyl-3-(2-thienyl) propanamine, hydrochloride

White crystals, 0.74 g: mp 165–166° C.; $^1$H NMR (CD$_3$OD) δ1.28 (d, 12H), 2.52 (m, 2H), 2.96 (m, 1H), 3.13 (m, 1H), 3.70 (br, 2H), 4.34 (t, 2H), 6.92–7.04 (m, 2H), 7.20–7.42 (m, 6H).

EXAMPLE 49

N-Cyclohexyl-N-methyl-3-phenyl-3-(2-thienyl) propanamine hydrochloride

White crystals, 1.1 g: mp 197–199° C.; $^1$H NMR (CD$_3$OD) δ1.15–1.52 (br, 5H), 1.68 (br, 1H), 1.90 (br, 4H), 2.51 (br, 2H), 2.78 (s, 3H), 2.91–3.40 (m, 3H), 4.31 (t, 1H), 6.92–7.04 (m, 2H), 7.20–7.40 (m, 6H).

EXAMPLE 50

N,N-Diethyl-3-phenyl-3-(2-thianyl)propanamine fumarate

White crystals, 1.7 g (tot. 49%): mp 135–137° C.; $^1$H NMR (CD$_3$OD) δ1.22 (t, 3H), 2.50 (m, 2H), 2.90–3.26 (m, 6H), 4.30 (t, 1H), 6.68 (s, 2H), 6.92–7.03 (m, 2H), 7.20–7.40 (m, 6H).

EXAMPLE 51

N-Isopropyl-N-methyl-3-phenyl-3-(2-thienyl) propanamine hydrochloride

White crystals, 1.6 g: mp 139–144° C.; $^1$H NMR (CD$_3$OD) δ1.24 (m, 6H), 2.52 (m, 2H), 2.75 (s, 3H), 3.03 (m, 2H), 3.59 (m, 1H), 4.32 (t, 1H), 6.92–7.04 (m, 2H), 7.20–7.40 (m, 6H).

EXAMPLE 52

N-[3-Phenyl-3-(2-thienyl)propyl]pyrrolidine fumarate

Crystallisation from 2-propanol, 1.1 g: mp 144–145° C.; $^1$H NMR (CD$_3$OD) δ2.02 (m, 4H) 2.31 (m, 2H), 2.97–3.42 (m, 6H), 4.29 (t, 1H), 6.69 (s, 2H), 6.91–7.01 (m, 2H), 7.18–7.38 (m, 6H).

EXAMPLE 53

N-[3-Phenyl-3-(2-thienyl)propyl]piperidine hydrochloride

The hydrochloride was crystallised from ethylmethylketone, 0.84 g: mp 193–194° C.; $^1$H NMR (CD$_3$OD) δ1.40–2.00 (b, 6H), 2.54 (m, 2H), 2.82–3.80 (m, 6H), 4.29 (t, 1H), 6.91–7.03 (m, 2H), 7.20–7.42 (m, 6H).

EXAMPLE 54

N,N-Diisopropyl-3-(2-hydroxy-5-methylphenyl)-3-(2-thienyl)propanamine hydrochloride White crystals, 2.1 g: mp 205–210° C.; $^1$H NMR (CDCl$_3$) δ1.36 (m, 12H), 2.18 (s, 3H), 2.63 (m, 2H), 2.95 (m, 2H), 3.54 (m, 4H), 4.61 (t, 1H), 6.76–7.01 (m, 5H), 7.16 (d, 1H).

EXAMPLE 55

(R*) N,N-Diisopropyl-3-(2-hydroxy-5-methylphenyl)-3-(2-thienyl)propanamine

To the racemic free base of N,N-diisopropyl-3-(2-hydroxy-5-methylphenyl)-2-thienylpropanamine (20 g, 0.06 mol), prepared in Example 54, in abs. ethanol (50 g) was added L-(+)-tartaric acid (9.5 g 0.063 mol) in ethanol (60 g). The salt formed was filtered off and crystallised twice from ethanol/methanol 10/1, 10 mL per gram of crystals, affording the title compound as white crystals, (6.8 g, 14.1 mmol): mp 214–215° C.; $[α]_{Hg}$=+17.3° (c=3.82 in methanol).

EXAMPLE 56

(S*) N,N-Diisopropyl-3-(2-hydroxy-5-methylphenyl)-3-(2-thienyl)propanamine

From the mother liquid from the first crystallisation to obtain (R*) N,N-diisopropyl-3-(2-hydroxy-5-methylphenyl)-3-(2-thienyl)propanamine in Example 55, the free base was recovered. The amine was treated with a 5% excess of D-(−)-tartaric acid in ethanol as above, yielding the title compound as white crystals, 6.1 g (12.7 mmol): mp 214° C.; $[α]_{Hg}$=−17.5° (c=3.85 in methanol).

EXAMPLE 57

N,N-Diisopropyl-3-phenyl-3-(3-thienyl) propanamine hydrochloride

White crystals, 0.94 g: mp 141–142° C.; $^1$H NMR (CDCl$_3$) δ1.42 (m, 12H), 2.87 (m, 4H), 3.56 (br, 2H), 3.98 (t, 1H), 6.94 (dd, 1H), 7.27 (m, 7H), 11.4 (br, 1H).

The starting compound was prepared as follows:

57.1 N,N-Diisopropyl-3-(3-thienyl)propenamide

Sodium hydride, 60% in mineral oil (3.9 g, 98 mmol), was washed several times with petroleum ether and dried under a stream of nitrogen. Sodium-dried THF was added followed by diethyl N,N-diisopropyl acetamidephosphonate (27.4 g, 98 mmol). When the evolution of gas had ceased, thiophene-3-aldehyde (10.0 g, 89.2 mmol) in THF(50 mL) was added at such a rate that the temperature never exceeded 45° C. After one hour of stirring at ambient temperature, the reaction was quenched with 4 mL of water and stirred for another hour. The solvent was evaporated and the residue was taken up in diethyl ether/2M NaOH. The organic phase was washed once with water and once with brine, dried (Na$_2$SO$_4$) and evaporated. The crude was chromatographed on silica (petroleum ether-ethyl acetate 4:1) affording the title compound as a light-brown oil, 14.8 g (70%): $^1$H NMR (CDCl$_3$) δ1.37 (b, 12H), 3.86 (br, 1H), 4.10 (br, 1H), 6.68 (d, 1H), 7.27–7.41 (m, 3H), 7.59 (d, 1H).

EXAMPLE 58

N,N-Diisopropyl-3-(2-furanyl)-3-phenylpropanamine hydrochloride

White crystals, 60 mg: mp 139–141° C.; $^1$H NMR (CDCl$_3$) δ1.41 (br, 12H), 2.64 (m, 1H), 2.85 (m, 3H), 3.55 (m, 2H), 3.98 (t, 1H), 6.16 (d, 1H), 6.31 (dd, 1H), 7.30 (m, 6H), 11.4 (br, 1H).

The starting compound was prepared as follows:

58.1 N,N-Diisopropyl-3-(2-furanyl)propenamide

The title compound was obtained from furfural with the procedure described in Example 57.1, as a colourless oil, 11.2 g (75%): $^1$H NMR (CDCl$_3$) δ1.32 (d, 12H), 4.0 (br, 2H), 6.41 (m, 2H), 6.76 (d, 1H), 7.38 (m, 2H).

EXAMPLE 59

N,N-Diisopropyl-3-(N-methylpyrrol-2-yl)-3-phenylpropanamine fumarate

A solution of N,N-diisopropyl-3-(N-methyl-pyrr-2-yl)-3-phenyl-propanamide (4.92 g, 15.7 mmol) in THF (75 mL), was dropped into a stirred mixture of LAH (2.38 g, 62.8 mmol). Stirring was continued at 50° C. overnight. Standard work-up gave the amine as a yellow oil, which was isolated as the fumarate salt, 2.74 g (42%): m.p. 134–6° C.; $^1$H NMR (CD$_3$OD) δ1.27 (d, 6H), 1.29 (d, 6H), 2.24 (m, 1H), 2.48 (m, 1H), 2.97 (dt, 1H), 3.26 (dt, 1H), 3,32 (s, 3H), 3.69 (septet, 2H), 4.08 (t, 1H), 6.05 (t, 1H), 6.16 (m, 1H), 6.57 (dd, 1H), 6.71 (s, 2H) and 7.19–7.34 (m, 5H).

The starting compound was prepared as follows:

59.1 N,N-Diisopropyl-3-(N-methylpyrrol-2-yl)-propenamide

The title compound was prepared from N-methyl-2-pyrrolaldehyde and N,N-diisopropyl-dimethylphosphon acetamide analogously to Example 4.2, giving 7.61 g (92%): $^1$H NMR(CDCl$_3$) δ1.32 (d, 6H), 1.35 (d, 6H), 3.68 (s, 3H), 4.00 (m, 2H), 6.13 (t, 1H), 6.55–6.66 (3H) and 7,57 (d, 1H).

59.2 N,N-Diisopropyl-3-(N-methylpyrrol-2-yl)-3-phenylpropanamide

The title compound was prepared from N,N-diisopropyl-3-(N-methylpyrrol-2-yl)-propenamide by a method analogous to that described in Example 41.3, giving 4.92 g (78%): $^1$H NMR (CDCl$_3$) δ0.85–1.32 (4d from rotamers, 12H), 2.91 (d, 2H), 3.31 (s, 3H) 3.45 (m, 1H), 3.88 (m, 1H), 4.65 (t, 1H), 6.07 (2H), 6.50 (dd, 1H) and 7.15–7.22 (5H).

EXAMPLE 60

3-(N-Methylpyrrol-2-yl)-3-phenyl-1-pyrrolidinopropane fumarate

The title compound was prepared analogously to Example 59, using N,N-tetramethylene-dimethylphosphon acetamide, yield 950 mg (36% tot.): m.p. 194–5° C.; $^1$H NMR (CD$_3$OD) δ1.27 (d, 12H), 2.2–2.6 (m, 2H) 3.05 (m, 2H), 3.66 (sept., 2H), 4.03 (t, 1H), 6.02 (two d, 2H), 6.64 (t, 1H), 6.69 (s, 2H) and 7.28 (m, 5H).

Biological Evaluation

The pharmacological activity of compounds prepared in the Examples was tested using in vitro methods.

Functional in Vitro Studies

Male guinea pigs, weighing about 300 g, were killed by a blow on the neck and exsanguinated. Smooth muscle strips of the urinary bladder were dissected in a Krebs-Henseleit solution (pH 7.4). The strip preparations were vertically mounted between two hooks in thermostatically controlled (37° C.) organ baths (5 ml). One of the hooks was adjustable and connected to a force transducer (FT 03, Grass Instruments). The Krebs-Henseleit solution was continuously bubbled with carbogen gas (93.5% O$_2$/6.5% CO$_2$) to maintain the pH at 7.4. Isometric tension was recorded by a Grass Polygraph (Model 79D). A resting tension of approximately 5 mN was initially applied on each muscle strip and the preparations were allowed to stabilise for at least 45 min. The resting tension was repeatedly adjusted and the preparations were washed several times during the stabilisation period.

Carbachol (carbamylcholine chloride) was used as the standard muscarinic receptor agonist. In each experiment, the viability of the preparations and the reproducibility of their contractile responses were initially tested by two consecutive additions of a submaximal concentration (3×10$^{-6}$ M) of carbachol. A concentration-response curve to carbachol was then generated by cumulative addition of carbachol to the organ-bath (i.e., stepwise increase of the agonist concentration until the maximal contractile response was reached), followed by washing out and a resting period of at least 15 min. before a fix concentration of the test compound (antagonist) was added to the organ-bath. After 60 min. of incubation with the antagonist, a second cumulative concentration-response curve to carbachol was generated. Responses were expressed as percent of the maximal response to carbachol. EC$_{50}$-values for carbachol in the absence (control) and presence of antagonist were graphically derived and dose ratios (r) were calculated. Dissociation constants, K$_B$, for the antagonists were calculated using equation (1) (Schild, H. I., Br. J. Pharmacol. Chemother. 1949, 4, 277–280), where [A] is the concentration of test compound:

$$K_B=[A]/r-1 \qquad (1)$$

The K$_B$ values obtained are presented in Table 1 below.

TABLE 1

| Example No. | K$_B$-value nM | Example No. | K$_B$-value nM | Example No. | K$_B$-value nM |
|---|---|---|---|---|---|
| 1 | 499 | 23 | 1.05 | 45 | 51 |
| 3 | 236 | 24 | 1.91 | 46 | 286 |
| 4 | 132 | 27 | 7.1 | 47 | 91 |
| 5 | 336 | 28 | 8.55 | 48 | 31 |
| 6 | 10 | 29 | 1.5 | 49 | 590 |
| 7 | 13 | 30 | 139 | 50 | 154 |
| 8 | 26 | 31 | 14 | 51 | 118 |
| 9 | 3.8 | 32 | 36 | 52 | 350 |
| 10 | 171 | 33 | 56 | 53 | 154 |
| 11 | 431 | 34 | 803 | 55 | 2 |
| 12 | 1.18 | 35 | 1773 | 56 | 360 |
| 13 | 15 | 36 | 2640 | 59 | 690 |
| 14 | 4.5 | 37 | 520 | 60 | 707 |
| 15 | 15 | 38 | 207 | | |
| 16 | 32 | 39 | 235 | | |
| 17 | 3.5 | 40 | 814 | | |
| 18 | 172 | 41 | 7.6 | | |
| 19 | 2.9 | 42 | 286 | | |
| 20 | 3315 | 43 | 29 | | |
| 22 | 2.8 | 44 | 2285 | | |

What is claimed is:

1. A compound of Formula (I):

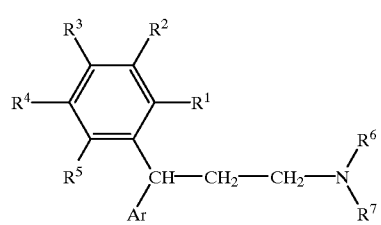

I wherein:
  R$^1$ is hydrogen, hydroxy, alkyl, alkoxy, hydroxyalkyl, trifluoromethyl, amino, alkylcarbonylamino, alkylcarbonyloxy, halogen,
  R$^2$ and R$^3$ independently are hydrogen, hydroxy, alkyl, alkoxy, hydroxyalkyl, halogen, alkoxycarbonylalkyl, carbamoyl, sulphamoyl,
  R$^4$ is ω-hydroxyalkoxy, ω-aminoalkoxy, ω-aminoalkylamino, alkoxyalkyl, hydroxyalkoxyalkylaminoalkyl, alkoxycarbonylalkyl, dihydroxyalkyl, formyl, alkylcarbonyl, alkoxycarbonyl, alkylcarbonylaminoalkyl, aminoalkyl, alkylaminoalkyl, dialkylaminoalkyl, carboxyalkyl, carbamoylalkyl, carboxamidoalkyl, carboxyl, amino, nitro, cyano, nitrilo, cyanoalkyl, azido, alkyl having two or more carbon atoms, alkoxy having two or more carbon atoms, hydroxyalkyl having two or more carbon atoms, $R^5$ is hydrogen, halogen, alkyl, Ar is aryl or heteroaryl wherein said aryl or heteroaryl are unsubstituted or independently substituted with one or two alkyl, alkoxy, hydroxy, hydroxyalkyl, halogen, alkoxycarbonylalkyl, carbamoyl, or sulphamoyl, and $R^6$ and $R^7$ are hydrocarbyl groups which are the same or different, together having three or more carbon atoms, and unsubstituted or substituted by one or more hydroxy groups, and wherein carbon atoms are or are not interconnected by oxygen atoms, and wherein $R^6$ and $R^7$ may or may not together form a ring with the amine nitrogen;

with the provisions that (a) when:
(i) two or more of $R^2$, $R^3$, and $R^5$ are other than hydrogen, or
(ii) $R^1$ is other than hydroxy or methoxy, and Ar is other than phenyl that is ortho-substituted by hydroxy or methoxy, or
(iii) Ar is heteroaryl, or
(iv) one or more of $R^6$ and $R^7$ is aromatic hydrocarbyl or cycloalkyl, then $R^4$ must be hydrogen, methyl, methoxy, hydroxymethyl, hydroxy, halogen, carbamoyl, or sulphamoyl;

and (b), when Ar is unsubstituted phenyl, then $R^1$, $R^2$, $R^3$, $R^4$ and $R^5$ can not all be hydrogen; and physiologically acceptable salts thereof, or the racemic mixture or the enantiomers thereof.

2. The compound according to claim 1, wherein $R^4$ is ω-hydroxyalkoxy, ω-aminoalkoxy, ω-aminoalkylamino, alkoxyalkyl, hydroxyalkoxyalkylaminoalkyl, dihydroxyalkyl, formyl, alkylcarbonyl, alkoxycarbonyl, alkoxycarbonylalkyl, alkylcarbonylaminoalkyl, aminoalkyl, alkylaminoalkyl, dialkylaminoalkyl, carboxyalkyl, carbamoylalkyl, carboxamidoalkyl, carboxyl, amino, nitro, cyano, nitrilo, cyanoalkyl, or azido.

3. The compound according to claim 2, wherein $R^1$ is hydrogen or methyl, $R^2$, $R^3$, and $R^5$ are either all hydrogen or one of $R^2$, $R^3$ and $R^5$ is methyl, methoxy, hydroxy, carbamoyl, sulphamoyl or halogen, and the others are hydrogen, and Ar is phenyl, said phenyl is unsubstituted or independently substituted with one or two methyl, methoxy, hydroxy, hydroxymethyl, carbamoyl, sulphamoyl or halogen.

4. The compound according to claim 1, wherein Ar is heteroaryl.

5. The compound according to claim 4, wherein $R^1$ is hydrogen or methyl, and $R^2$, $R^3$, $R^4$ and $R^5$ are either all hydrogen or one of $R^2$, $R^3$, $R^4$ and $R^5$ is methyl, methoxy, hydroxy, hydroxymethyl, carbamoyl, sulphamoyl or halogen, and the others are hydrogen.

6. The compound according to claim 1, wherein $R^1$ is hydrogen, alkyl, hydroxyalkyl, trifluoromethyl, amino, alkylcarbonylamino, alkylcarbonyloxy, or halogen, and Ar is other than phenyl that is ortho-substituted by hydroxy or alkoxy.

7. The compound according to claim 6, wherein $R^1$ is hydrogen or methyl, $R^2$, $R^3$, $R^4$ and $R^5$ are either all hydrogen or one of $R^2$, $R^3$, $R^4$ and $R^5$ is methyl, methoxy, hydroxy, carbamoyl, sulphamoyl or halogen, and the others are hydrogen, and Ar is phenyl, said phenyl is unsubstituted or independently substituted with one or two methyl, methoxy, hydroxy, hydroxymethyl, carbamoyl, sulphamoyl or halogen.

8. The compound according to claim 1, wherein one or more of $R^6$ and $R^7$ is aromatic hydrocarbyl, cycloalkyl or a hydrocarbyl chain, wherein carbon atoms are interconnected by an oxygen atom in one or more position on said aromatic hydrocarbyl, said cycloalkyl or said hydrocarbyl chain.

9. The compound according to claim 8, wherein $R^1$ is hydrogen or methyl, $R^2$, $R^3$, $R^4$ and $R^5$ are either all hydrogen or one of $R^2$, $R^3$, $R^4$ and $R^5$ is methyl, methoxy, hydroxy, carbamoyl, sulphamoyl or halogen, and the others are hydrogen, and Ar is phenyl, said phenyl is unsubstituted or independently substituted with one or two methyl, methoxy, hydroxy, hydroxymethyl, carbamoyl, sulphamoyl or halogen.

10. The compound according to claim 1, wherein $R^1$ is hydroxy, halogen, trifluoromethyl, amino, methoxy or hydroxymethyl.

11. The compound according to claim 1, wherein $R^2$ and $R^3$ independently are hydrogen, hydroxy or hydroxymethyl.

12. The compound according to claim 1, wherein $R^4$ is hydrogen, formyl, alkoxycarbonyl, alkylcarbonyl, hydroxyalkyl, alkoxyalkyl, carboxamidoalkyl, carbamoylalkyl, aminoalkyl, amino, azido, cyanoalkyl, carboxy or carboxyalkyl.

13. The compound according to claim 12, wherein $R^4$ is hydrogen, formyl, hydroxymethyl, hydroxyethyl, hydroxypropyl, hydroxybutyl, hydroxypentyl, hydroxyhexyl, ethoxymethyl, methoxycarbonyl, amino, aminopropyl, acetyl, 1,2-hydroxyethyl, ethylaminomethyl, or hydroxyethoxyethyl-aminoethyl.

14. The compound according to claim 1, wherein $R^5$ is hydrogen.

15. The compound according to claim 1, wherein each of $R^6$ and $R^7$ independently signify a saturated hydrocarbyl group $R_6$ and $R_7$ together containing at least three or more.

16. The compound according to claim 1, wherein $R^6$ and $R^7$ taken together form a ring with the amine nitrogen.

17. The compound according to claim 1, wherein one or more of $R^6$ and $R^7$ is a branched carbon chain.

18. The compound according to claim 1, wherein Ar is thienyl, pyrryl, thiazolyl, oxazolyl, methylthiazolyl or methylpyrryl.

19. The compound according to claim 1, which is:

N,N-diisopropyl-3-(2-fluorophenyl)-3-phenylpropanamine hydrochloride,

N,N-diisopropyl-3-(5-formyl-2-hydroxy-phenyl)-3-phenylpropanamine, or its (R)-isomer, N,N-diisopropyl-3-(2-hydroxy-5-methyloxycarbonylphenyl)-3-phenylpropanamine, or its (R)-isomer, N,N-diisopropyl-3-(5-acetyl-2-hydroxyphenyl)-3-phenylpropanamine, or its (R)-isomer, N,N-diisopropyl-3-[2-hydroxy-5-(2-hydroxyethyl)phenyl]-3-phenylpropanamine, or its (R)-isomer, N,N-diisopropyl-3-[2-hydroxy-5-(1-hydroxyethyl)phenyl]-3-phenylpropanamine, or its 3(R)-isomer, N,N-diisopropyl-3(R)-[5-(1(R*),2-dihydroxyethyl)-2-hydroxyphenyl]-3-phenylpropanamine, or its 1(S*)-isomer, N,N-diisopropyl-3-[2-hydroxy-5-(6-hydroxyhexyl)phenyl]-3-phenylpropanamine, or its (R)-isomer, N,N-diisopropyl-3-(5-ethoxymethyl-2-hydroxyphenyl)-3-phenylpropanamine, or its (R)-isomer, N,N-diisopropyl-3-[5-(3-aminopropyl)-2-hydroxyphenyl]-3-phenylpropanamine, or its (R)-isomer, N,N-diisopropyl-3-[5-(3-acetamidopropyl)-2-hydroxyphenyl]-3-phenylpropanamine, or its (R)-isomer, N,N-diisopropyl-3-[5-(2-cyanoethyl)-2-hydroxyphenyl]-3-phenylpropanamine, or its (R)-isomer, N,N-diisopropyl-3-(5-amino-2-hydroxyphenyl)-3-phenylpropanamine, or its (R)-isomer, N,N-diisopropyl-3-(5-azido-2-hydroxyphenyl)-3-phenylpropanamine, or its (R)-isomer, N,N-diisopropyl-3-[2-hydroxy-5-(3-hydroxypropyl)phenyl]-3-phenylpropanamine, or its (R)-isomer, N-cyclobutyl-N-methyl-3-(2-hydroxyphenyl)-3-phenylpropanamine, N,N-diisopropyl-3-(2-hydroxyphenyl)-3-(2-thienyl)propanamine, or N,N-diisopropyl-3-(2-hydroxy-5-methylphenyl)-3-(2-thienyl)propanamine, or its (R)-isomer.

20. A pharmaceutical composition, comprising:
a compound according to claim 1 and a compatible pharmaceutical carrier.

21. A method of treating a patient suffering from urinary incontinence, which method comprises the step of administering to said patient an effective amount of a compound according to claim 1.

22. A method for the treatment of a patient suffering from an acetylcholine-mediated disorder, which method comprises the step of:
administering to said patience an effective amount of a compound according to claim 1.

23. A method of preparing the compound of Formula (I) according to claim 1, which comprises:

a) reacting a compound of Formula II with an amine HNR⁶R⁷, wherein R⁶ and R⁷ are as defined above,

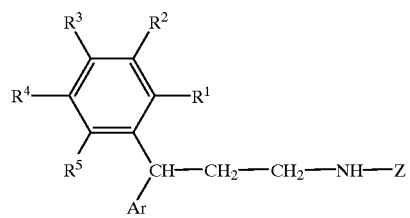

II wherein $R^1$ to $R^5$ and Ar are as defined in claim 1, and Y is a leaving group, or b) reducing a compound of Formula III

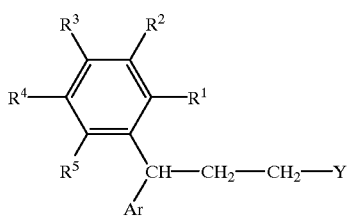

III wherein $R^1$ to $R^7$ and Ar are as defined in claim 1 and any hydroxy groups present on the compound of Formula (III) are protected, or c) N-alkylating a secondary amine of Formula IV

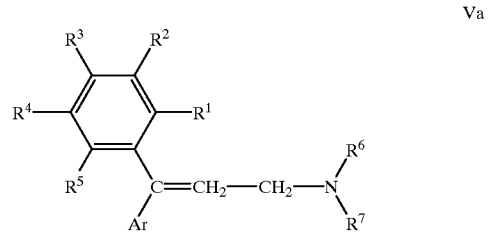

IV wherein $R^1$ to $R^5$ and Ar are as defined in claim 1 and any hydroxy groups present on the compound of Formula (III) are protected, and wherein Z has the same meaning as $R^6$ and $R^7$, or d) reducing a compound of Formula Va or Vb

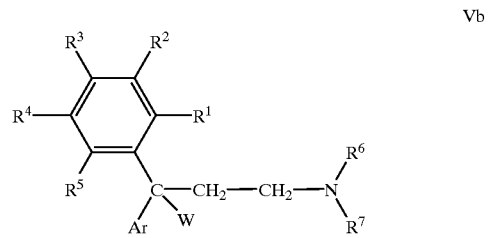

Va

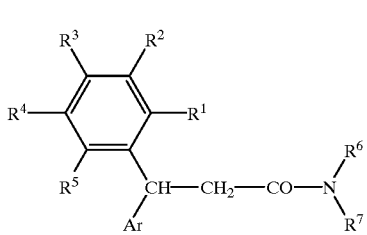

Vb wherein $R^1$ to $R^7$ and Ar are as defined in claim 1 and any hydroxy groups present on the compound of Formula (III) are protected, and W signifies a hydroxy group or halogen, or ei) converting $R^1a$ to hydroxymethyl in a compound of Formula VI, wherein $R^2$ to $R^7$ and Ar are as defined above in claim 1, and $R^1a$ is carboxyl, when the transformation is a simple reduction, or eii) converting $R^1a$ to a hydroxy in a compound of Formula VI, wherein $R^2$ to $R^7$ and Ar are as defined in claim 1, and $R^1a$ is alkoxy, when the reaction is a reductive dealkylation or a Lewis acid induced dealkylation,

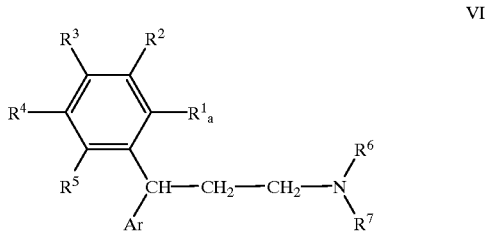

VI or f) reducing an alkylene to alkyl, hydroxyalkyl or dihydroxyalkyl, in a compound of Formula VII

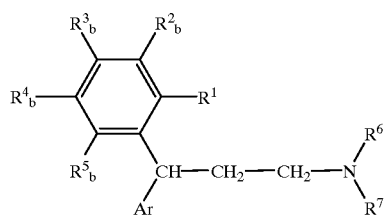

wherein $R^1$, $R^6$, $R^7$, and Ar are as defined in claim 1, and one of $R^2b$ to $R^5b$ is alkylene and the others are as defined in claim 1 for $R^2$ to $R^5$, or g) reacting a compound of Formula VIII with a compound of Formula IX to form a compound of Formula Ia

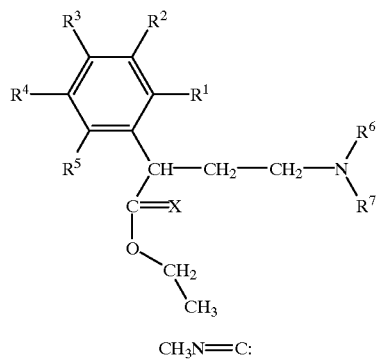

CH₃N≡C:

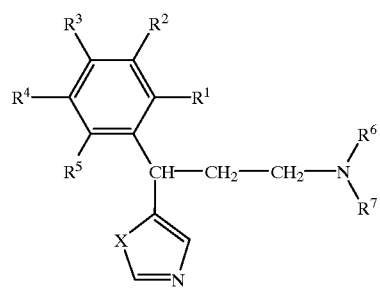

wherein $R^1$ to $R^7$ are as defined in claim 1, and X is oxygen or sulphur, or h) reacting a compound of Formula VIII above, wherein X is oxygen, with a compound of Formula X to form a compound of Formula Ib

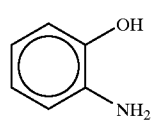

-continued

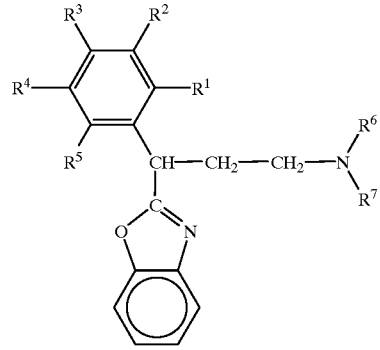

wherein $R^1$ to $R^7$ are as defined in claim 1, or i) converting a compound of Formula XI to a compound of Formula XII by reacting a compound of Formula XI with formamide, then reducing the product to form Formula XII

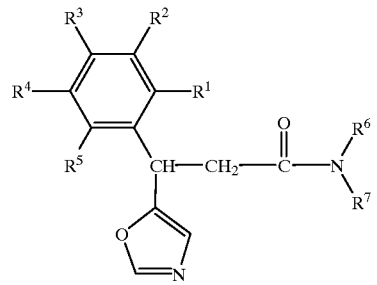

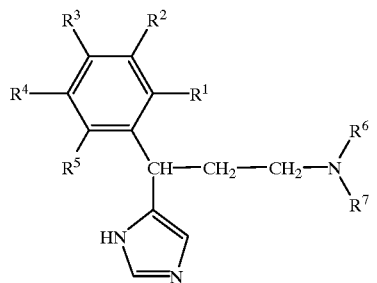

wherein $R^1$ to $R^7$ are as defined in claim 1, or j) converting a compound of Formula XIII to a compound of Formula XIV by reacting a compound of Formula XIII in formic acid with a suitable substrate to form a compound of Formula XIV

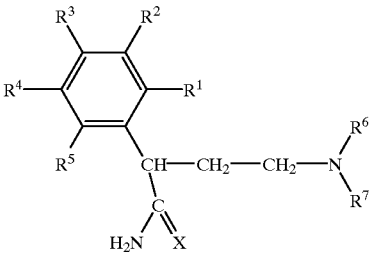

-continued

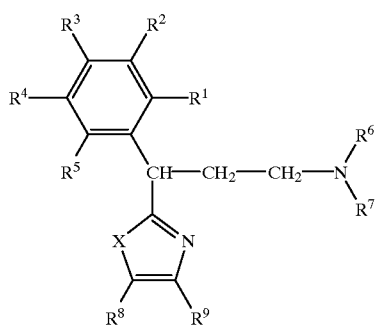

XIV wherein $R^1$ to $R^7$ are as defined in claim 1, and X is oxygen or sulphur, and $R^8$ and $R^9$ independently are hydrogen or alkyl.

24. The compound according to claim 15, wherein each of $R^6$ and $R^7$ independently signify a saturated aliphatic $C_{1-8}$alkyl.

25. The compound according to claim 15, wherein each of $R^6$ and $R^7$ independently signify a saturated aliphatic $C_{1-6}$alkyl, or adamantyl.

26. The compound according to claim 15, $R_6$ and $R_7$ together having four or more carbon atoms.

27. The pharmaceutical composition according to claim 20, whereby the daily dose of the active compound is from about 0.01 mg to about 4 mg per kilo of body weight.

28. The pharmaceutical composition according to claim 27, whereby the active compound is administered singly in a dose of from about 0.05 mg to about 200 mg.

29. The pharmaceutical composition according to claim 27, whereby the active compound is administered multiply in a dose of from about 0.05 mg to about 200 mg.

30. The method according to claim 21, wherein said urinary incontinence disorder is urge incontinence.

31. The method of preparing the compound of Formula (I) according to claim 23, further comprising removing hydroxy protecting groups from the obtained compounds.

32. The method of preparing the compound of Formula (I) according to claim 23, further comprising adding physiological acceptable acids to obtained bases of Formula (I) to form the salts thereof.

33. The method of preparing the compound of Formula (I) according to claim 23, further comprising separating the resulting optical isomers of Formula (I) into the individual enantiomers.

* * * * *

UNITED STATES PATENT AND TRADEMARK OFFICE
CERTIFICATE OF CORRECTION

PATENT NO. : 6,313,132 B1
DATED : November 6, 2001
INVENTOR(S) : Rolf Johansson et al.

It is certified that error appears in the above-identified patent and that said Letters Patent is hereby corrected as shown below:

<u>Title page,</u>
Item [75], Inventors, please correct the fourth inventor's name from "Ian Vagberg" to
-- Jan Vagberg --.
Please insert Item [30], Foreign Application Priority Data, as follows:
-- [30] Foreign Application Priority Data,
Mar. 27, 1997   (SE) .. .. .. .. .. .. .. .. .. .. .. 9701144-9 --.

Signed and Sealed this

Thirteenth Day of August, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.     : 6,313,132 B1
DATED          : November 6, 2001
INVENTOR(S)    : Rolf Johansson et al.

It is certified that error appears in the above-identified patent and that said Letters Patent is hereby corrected as shown below:

Title page,
Please insert Item [30], Foreign Application Priority Data, as follows:
-- [30]  Foreign Application Priority Data,
Mar. 27, 1997   (SE) .. .. .. .. .. .. .. .. .. .. .. 9701144-9 --.

Signed and Sealed this

Twelfth Day of August, 2003

JAMES E. ROGAN
*Director of the United States Patent and Trademark Office*